(12) United States Patent
Wu et al.

(10) Patent No.: US 8,343,922 B2
(45) Date of Patent: Jan. 1, 2013

(54) COMPOSITIONS AND METHODS FOR THE STIMULATION OR ENHANCEMENT OF BONE FORMATION AND THE SELF-RENEWAL OF CELLS

(75) Inventors: Dianqing Wu, Chesire, CT (US); Xiaofeng Li, West Hartford, CT (US); Peng Liu, West Hartford, CT (US); Wenzhong Liu, Farmington, CT (US); Dean Engelhardt, New York, NY (US)

(73) Assignee: Enzo Biochem, Inc., Farmingdale, NY (US)

( * ) Notice: Subject to any disclaimer, the term of this patent is extended or adjusted under 35 U.S.C. 154(b) by 729 days.

(21) Appl. No.: 10/849,643

(22) Filed: May 19, 2004

(65) Prior Publication Data

US 2005/0261181 A1 Nov. 24, 2005

(51) Int. Cl.
*A61K 38/00* (2006.01)
*A61P 19/08* (2006.01)
*A61P 19/10* (2006.01)

(52) U.S. Cl. ...................................... 514/16.7; 514/16.9
(58) Field of Classification Search .......................... None
See application file for complete search history.

(56) References Cited

U.S. PATENT DOCUMENTS

| | | |
|---|---|---|
| 6,844,422 B1 | 1/2005 | Niehrs et al. |
| 2003/0165500 A1 | 9/2003 | Rhee |
| 2003/0181660 A1 | 9/2003 | Todd et al. |
| 2004/0009535 A1 | 1/2004 | Brunkow |
| 2004/0023356 A1 | 2/2004 | Krumlauf |
| 2004/0038860 A1 | 2/2004 | Allen |
| 2004/0235728 A1* | 11/2004 | Stoch et al. ............... 514/12 |
| 2005/0084494 A1* | 4/2005 | Prockop et al. ............ 424/146.1 |
| 2005/0196349 A1 | 9/2005 | Wu et al. |
| 2005/0261181 A1 | 11/2005 | Wu et al. |
| 2006/0030523 A1 | 2/2006 | Wu et al. |
| 2006/0127393 A1 | 6/2006 | Li et al. |
| 2006/0257892 A1 | 11/2006 | Cohen et al. |
| 2008/0119402 A1 | 5/2008 | Zheng et al. |

OTHER PUBLICATIONS

Johnson et al., Journal of Bone and Mineral Research Nov. 2004, vol. 19, No. 11: 1749-1757.*
Zhang et al., Mol. Cell. Biol. 2004 24: 4677-4684.*
U.S. Appl. No. 09/356,294, filed Jul. 16, 1999, Rabbani et al.
U.S. Appl. No. 08/574,443, filed Dec. 15, 1995, Rabbani et al.
U.S. Appl. No. 60/965,279, filed Aug. 17, 2007.
2001 NIH Consensus Conference Development Panel on Osteoporosis Prevention, Diagnosis and Therapy. JAMA 285:785-795.
Axford, John S. Glycobiology & Medicine: A Millenial Review, Jul. 11-12, 2000 lecture at 5th Jenner Symposium held at Royal Society of Medicine, London, UK, http://www/glycoscience.com/glycoscience/document_viewer.wm?FILENAME=D006.
Babij et al., 2003, J Bone Miner Res 18:960-74.
Bafico et al., 2001, Nat Cell Biol 3:683-6.
Bain et al., 2003, Biochem Biophys Res Commun 301:84-91.
Barrandon, Yann Mar. 20, 2003, Nature vol. 422:272-273.
Boyden et al., May 16, 2002, N. Engl J Med 346(20):1513-21.
Capelluto et al. 2002, Nature 419(6908):726-9.
Cheyette et al. 2002, Dev Cell, vol. 2, 449-461.
Culi et al. 2003, Cell 112:343-54.
Dann et al. 2001, Nature, vol. 412, 86-90.
Erickson et al. Mar. 1973, Journal of Lipid Research, vol. 14:133-137.
Gao, Yuan et al., May 18, 2004, PNAS, vol. 101, No. 20, pp. 7618-7623.
Glinka et al, 1998, Nature 391(6665):357-62.
Glinka et al, Jun. 10, 2002, DKFZ 2001: Research Report 1999/2000: 36-40.
Gong et al. 2001, Cell 107:513-23.
Gumbiner et al. 1998, 8:430-5 Curr Opin Genet Dev.
Guo, Nini et al. Jun. 22, 2004, vol. 101, No. 25, pp. 9277-9281.
Graham et al. 2000 Cell. 103(6):885-96.
Gruneberg, et al. 2001, Angew. Chem. Int. Ed Engl. 40, 389-393.
Hey et al. 1998. Gene 216, 103-11.
Hsieh et al. 2003, Cell 112:355-67.
Hsu et al. 1998, Molecular and Cellular Biology 18:4807-4818.
Hurst 1994 J. Chem. Inf. Comput. Sci. 34, 190-196.
Jeon et al. 2001, Nat Struct Biol 8:499-504.
Kalajzic et al. 2002, J Bone Miner Res 17(1):15-25.
Kannus et al. 2000, Osteoporos Int 11:443-8.
Kato et al. 2002, J Cell Biol 157(2):303-14.
Krupnik et al. 1999, Gene 238:301-13.
Leyns et al. 1997, Cell, vol. 88, 747-756.
Li et al. 2002, J Biol Chem 277(8):5977-81.
Li et al. 1999, EMBO J 18:4233-4240.
Li et al. 1999, J. Biol. Chem. 274:129-134.
Lilien, Ryan H. et al., Mar. 4, 2004 Dartmouth Computer Science Dept. Technical Report No. TR2004-492 at http://www.cs.dartmouth.edu/reports/reports.html.
Lips, 1997, Am J Med 103:3S-8S; discussion 8S-11S.
Little et al. 2002, Am J Hum Genet 70:11-9.
Love et al, 1995, Nature. 376(6543):791-5.
Mao et al. 2002, Nature 417:664-7.
Mao et al, Nature vol. 411:391-5.
Mao et al, 2001, Mol Cell 7:801-9.
Monaghan 1999, Mech Dev 87:45-56.

(Continued)

*Primary Examiner* — Daniel C Gamett
(74) *Attorney, Agent, or Firm* — Elie Gendloff, Esq.

(57) ABSTRACT

Compositions and methods for the treatment of bone diseases, bone fractures, bone injuries and other bone abnormalities involving the use of Dkk protein, a Wnt antagonist, a Wnt inhibitor, or any other related protein for the stimulation or enhancement of mineralization and for stimulating the renewal of cells. One Dkk protein, Dickkopf-2 (Dkk-2), acts to stimulate bone formation independently of Wnt proteins which may be inhibited and/or antagonized by Dkk-2. Dkk-2 displayed enhanced specific targeting ability and enhanced biological activity in stimulating or enhancing mineralization. Dkk-2 also played a role in the differentiation and self-renewal of hematopoietic stem cells and mesenchymal stem cells, particularly in osteoblastogenesis and osteoclastogenesis.

15 Claims, 12 Drawing Sheets

OTHER PUBLICATIONS

Moon RT et al, 1997, Cell, vol. 88, 725-728.
Nusse 2001, Nature 411:255-6.
Pandur et al, 2001, Bioessays 23:207-10.
Pfaffl 2001, Nucleic Acids Res May 1, 2001;29(9):e45.
Pinson et al, 2000, Nature 407:535-538.
Poy 2001, Nat Struct Biol. 8(12):1053-7.
Rarey et al, 1996 J. Mol. Biol. 261: 470-479.
Reddy, Seshamma T., et al. 2004 J Invest Dermatol 123:275-282.
Schweizer et al, 2003, BMC Cell Biol 4:4.
Semenov et al, 2001, Curr Biol 11: 951-61.
Szilagyi, Andras et al., Phys.Biol. 2 (2005) 1-16.
Takagi et al, 2003, Nature 424:969-74.
Tamai et al, 2000, Nature 407:530-5.
Tamai et al, 2004, Molecular Cell, vol. 13, 149-156.
Tolwinski et al, 2003, et al, Dev Cell 4:407-18.
Toogood, Peter L. Apr. 11, 2002, Journal of Medicinal Chemistry vol. 45, No. 8, pp. 1543-1558.
Van Wesenbeeck et al, 2003, Am J Hum Genet 72:763-71.
von Kries et al, 2000, Nat Struct Biol. 7(9):800-7.
Waszkowycz, et al, 2001, IBM Systems J. 40, 360-376.
Wang, et al., 2005 Journal of Medicinal Chemistry, vol. 48, No. 7, 2432-2444.
Wehrli, et al, 2000, Nature 407:527-30.
Wharton 2003, Dev Biol. 253(1):1-17.
Wodarz 1998, Annu. Rev. Cell Dev. Biol. 14:59-88.
Wong et al, 2003, Mol Cell. 12(5):1251-60.
Wong et al, 2000, Nat Struct Biol. 7(12):1178-84.
Xing Y et al, 2003, Genes Dev. Nov 15, 2003;17(22):2753-64.
Wang et al., Am Chem Society, 2004.
Zuckerman 1996, N Engl J Med 334:1519-25.
Reya et al, 2005 Nature 434: 843.
Kleber et al, 2004 Curr Opin Cell Biol 16:681.
Logan et al, 2004 Annu Rev Cell Dev Biol 20: 781.
Sancho et al, 2004 Annu Rev Cell Dev Biol 20: 695-723.
Wang et al, 2004 Curr Opin Genet Dev 14: 533.
Moon et al, 2004, Nat Rev Genet 5:691.
Kawano et al, 2003, J Cell Sci 116: 2627.
Zhang et al., 2004, Mol Cell Biol 24:4677-4684.
Fujino et al., 2003, Proc Natl Acad Sci USA 100: 229.
Yamazaki et al, 2003, Biochem Biophys Res Commun 304: 229.
Hoffmann et al., 1999, J Med Chem 42: 4422.
Kramer 1999, Proteins 37: 228.
Mundy et al., 1999, Science 286: 1946.
Dunstan et al., 1999, J Bone Miner Res 14:953.
Li, et al, 2001, Cell Mol Life Sci 58: 2085.
Smith, 1999, Trends Biochem Sci 24: 181.
Yuan et al, 1999, J. Biol. Chem. 274: 30419-30423.
Li et al, 2002, JBC 277; 5977-5981.
Li et al., 2005, JBC vol. 280, No. 20, 19883-19887.
Wei et al. 2006, Cell 124; 1141-1154.
Johnson et al., 2004, J Bone Disease and Mineral Research 19; 1749-1757.
Hay et al. 2005, JBC 280; 13616-13623.
Kikuchi et al., 2006, Exp Molec. Med 38; 1-10.
Semenov et al. 2005, JBC 280; 26770-26775.
Streeten et al., 2008, Bone 43(2008) 584-590.
Krane 2005, J Exp Med 201; 841-843.
Krishnan et al., 2006, J Clin Invest 116; 1202-1.
Liang et al., 2003, Cancer Cell 4:349-360.
Weeraratna et al., 2002, Cancer Cell 1:279-288.
Polakis 2000 Genes Dev 14: 1837-1851.
Behrens and Lustig 2004 Int J Dev Biol 48: 477-487.
Luu et al., 2004 Curr Cancer Drug Targets 4; 653-671.
Bafico et al., 2004 Cancer Cell 6; 497-506.
Janssens et al., 2006 Investigational New Drugs 24; 263-280.
Tian et al. 2003 NEJM 349: 2483-2494.
Oshima et al., 2005 Blood 106: 3160-3165.
Toomes et al, 2004 Am. J. Hum. Genet. 74: 751-730.
Niemann et al., 2004 Am J. Hum. Genet 74: 558-563.
Grant et al., 2006, Nature Genetics 38: 320-323.
Rodova et al., 2002 J. Biol. Chem 277: 29577-29583.
Surendran et al., Am J Physiol Renal Physiol 282: F431-F441, 2002.
Chilosi et al., 2003, Am J. Pathol. 162: 1495-1502.
Cheon et al., 2002 Proc. Nat, Acad. Sci. (USA) 99: 6973-6978.
Miyaoka et al., 1999 Schizophr. Res. 38:1-6.
Symolon et al. 2004 J. Nutr. 134: 1157-1161.
Chen H. et al. Cell 84: 491-495, 1996.
Lee G.H. Nature 379: 632-635, 1996.
Nusse and Varmus 1982, Cell 31:99-109.
Couso et al., 1995 Development 120: 621-636.
Mukhopadhyay et al., 2001 Dev Cell 1:423-434.
Li et al., 2005 Nature Genetics 37:945-952.
Mukhopadhyay et al., 2006 Development 133:2149-2154.
Pinson et al., 2000 Nature 407:535-538.
Magoori et al., 2003 J Biol Chem 278:11331-11336.
Van Amerongen and Burns, 2006 Trends Genet 12:678-389.
Bockamp et al., 2002 Physiol Genomics 11:115-132.
Raport et al., 1996 J. Biol Chem 271:17161-17166.
Deng et al., 1996 Nature 382:661-666.
Dragic et al., 1996 Nature 381-667-673.
Abrami et al., 2003 J. Cell Biol 160:321-328.
Bradley et al., 2001, Nature 414:225-229.
Scobie et al., 2003 Proc Nat Acad Sci USA 100:5170-5174.
Molloy et al., 1992 J. Biol Chem 267:16396-16402.
Petosa et al., 1997 Nature 385:833-838.
Chauhan and Bhatnagar 2002, Infect Immunol 70:4477-4484.
Cunningham et al., 2002 Proc Nat Acad Sci USA 99:7049-7083.
Pannifer et al., 2001 Nature 414:229-233.
Elliot et al., 2000 Biochemistry 39:6706-6713.
Lacy et al.,2002 J. Biol. Chem. 277:3006-3010.
Rosovitz et al., 2003 J. Biol. Chem. 278:30936-30944.
Little et al., 1988 Infect Immun 56:1807-1813.
Lacy et al., 2004 Proc Nat Acad Sci USA 13147-13151.
Liu et al., Apr. 2007 Cell Microbiol 9(4):977-987.
Moayeri et al., 2006 Antimicrob Agents and Chemotherapy 50:2658-2665.
Schepetkin et al., 2006 J. Med. Chem. 49:5232-5244.
Goldman et al., 2006 BMC Pharmacology 6:8-15.
Panchal et al., 2004 Nat Struct Mol Biol 11:67-72.
Forino et al., 2005 Proc Nat Acad Sci USA 102:9499-9504.
Johnson et al., 2006 J. Med. Chem. 12:27-30.
Turk et al., 2004 Nat Struct Mol Biol 11:60-66.
Kocer et al., 2005 Infection and Immunity 73:7548-7557.
Karginov et al., 2005 Proc Nat Acad Sci USA 102:15075-15080.
Opal et al., 2005 Infect Immun 73:5101-5105.
Komiyama et al., 2005 Antimicrob Agents Chemotherapy 49:3875-3882.
Basha et al., 2006 Proc Nat Acad Sci USA 103:13509-13513.
E.L. Eliel & S.H. Wilen, Stereochemistry of Carbon Compounds, John Wiley & Sons, New York, NY, 1994, pp. 1119-1190.
Simon-Chazottes et al., 2006 Genomics 87:673-677.
Erlanson et al., 2004 J. Med Chem. 47:3463-3482.
Erlanson, 2006 Curr Opin Biotech 17:643-652.
Morrisey, 2003 Am J Path 162:1393-1397.
Pongracz and Stockley 2006 Respiratory Research 7:15.
Tickenbrock 2006 J Leuk Biol 79:1306-1311.
Figueroa et al., 2000 J. Histochem & Cytochem, 48(10):1357-1368.
Sen et al., 2000 Proc Nat Acad Sci USA 2791-2796.
Nakamura et al., 2005 am J Path 167:97-105.
Gustafson and Smith 2006 J. Biol Chem 281:9507-9516.
Cawthom et al., 2007 Cell Death Differ 14:1361-1373.
Diarra et al., 2007 Nature Medicine 13:156-163.
Rothbacher and Lemaire 2002 Nature Cell Biology 4:E172-E173.
Liu et al., 2003 Molec and Cell Biol 23:5825-5835.
Andl et al., 2002 Developmental Cell 2:643-653.
Sick et al., 2006 Science 1447-1450.
Papakonstantinou et al., J. Invest Dermatol 125:673-684, 2005.
Tamamura et al., 2005 J. Biol. Chem. 280:19185-19195.
Hertz and Strickland, 2001 J. Clin. Invest. 108:779-784.
Zeng et al. 2008 Development 135:367-375.
Nam et al., 2006 JBC 281(19):13247-13257.
Mercurio et al., 2003 Development 131:2137-2147.
Davidson et al., Nature 438:867-872, 2005.
Swiatek et al., 2006 J Biol Chem 281:12233-12241.

Zilberberg et al., 2004 J. Biol Chem 279:17535-17542.
Guo et al., 2006 J Med Genet 43:798-803.
Mani et al., 2007 Science 315:1278-1282.
He et al., 2005 Development 131:1663-1677.
Wu et al., 2000, Curr Biol 10:1611-1614.
Zorn, 2001, Curr Biol 11:R592-R595.
Brott and Sokol, 2002 Molec and Cell Biol 22:6100-6110.
Mikels and Nusse, 2006 PloS 4:0570-0582.
Johnson et al., 2006 Genomics 88:600-609.
Pukrop et al., 2006 Proc Natl Acad Sci USA 103:5454-5459.
Lin et al., 1994 Anal Record 240:492-506.
Miyauchi et al., 2001 Histochem Cell Biol 116:57-62.
Elbashir, S. M. et al. Duplexes of 21-nucleotide RNAs mediate RNA interference in cultured mammalian cells. *Nature* 411, 494-8 (2001).
Brummelkamp, T. R., Bernards, R. & Agami, R. A system for stable expression of short interfering RNAs in mammalian cells. *Science* 296, 550-3 (2002).
Kahler, R. A. & Westendorf, J. Lymphoid enhancer factor-1 and beta-catenin inhibit Runx2-dependent transcriptional activation of the osteocalcin promoter. *J Biol Chem* vol. 278, No. 14, 11937-44 (2003).
Mundlos, S. et al. Mutations involving the transcription factor CBFA1 cause cleidocranial dysplasia. *Cell* 89, 773-9 (1997).
Otto, F. et al. Cbfa1, a candidate gene for cleidocranial dysplasia syndrome, is essential for osteoblast differentiation and bone development. *Cell* 89, 765-71 (1997).
Komori, T. et al. Targeted disruption of Cbfa1 results in a complete lack of bone formation owing to maturational arrest of osteoblasts. *Cell* 89, 755-64 (1997).
Ducy, P., Zhang, R., Geoffroy, V., Ridall, A. 1. & Karsenty, G. Osf2/Cbfa1 : a transcriptional activator of osteoblast differentiation. *Cell* 89, 747-54 (1997).
Pandur, P., Lasche, M., Eisenberg, 1. M. & Kuhl, M. Wnt-11 activation of a non-canonical Wnt signaling pathway is required for cardiogenesis. *Nature* 418, 636-41 (2002).
Zhang, J, et al. Identification of the haematopoietic stem cell niche and control of the niche size. Nature 425, 836-841 (2003).
Itoh, K., Antipova, A., Ratcliffe, M. J. & Sokol, S. Interaction of dishevelled and Xenopus axin-related protein is required for Wnt signal transduction. *Mol Cell Biol* vol. 20, No. 6, 2228-38 (2000).
Calvi, L, et al. Osteoblastic cells regulate the haematopoietic stem cell niche. Nature 425, 841-846 (2003).
Li, Song et al., A computer screening approach to immunoglobulin superfamily atructures and interactions: Discovery of small non-peptidic CD4 inhibitors as novel immunotherapeutics, Proc Natl Acad Sci USA vol. 94, pp. 73-78, Jan. 1997.
Willert, K, et al. Wnt proteins are lipid-modified and can act as stem cell growth factors. Nature 423, 448-452 (2003).
Gregory, C, et al. The Wnt signaling inhibitor Dickkopf-1 is required for re-entry into the cell cycle of human adult stem cells from bone marrow. The Journal of Biological Chemistry 278, (30):28067-28078 (2003).
Teitelbaum, S, et al. Genetic Regulation of osteoclast development and function. Nature Genetics 4, 638-649 (2003).

Prockop, D, et al. One strategy for cell and gene therapy: Harnessing the power of adult stem cells to repair tissues. PNAS 100, Supp. 1, 11917-11923 (2003).
Brossay, L. et al. CD1d-mediated recognition of an α-galactosylceramide by natural killer T cells is hightly conserved through mammalian evolution. J. Exp. Med. 188,(8): 1521-1528 (1998).
Van der Vliet, H., et al. Potent expansion of human natural killer T cells using α-galactosylceramide (KPN7000)-loaded monocyte-derived dendritic cells, cultured in the presence of IL-7 and IL-15. J. Immunol. Methods 247, 61-72 (2001).
Taichman R.,et al. The Hematopoietic Microenvironment: Osteoblasts and the Hematopoietic Microenvironment. Hematol. 4(5):421-426 (2000).
Rattner A, et al. A family of secreted proteins contains homology to the cysteine-rich ligand-binding domain of frizzled receptors. PNAS. 94(7):2859-63. (1997).
Yamane T., et al. Wnt Signaling Regulates Hemopoiesis through Stromal Cells. J. Immunology. 167:765-772. (2001).
Johnson et al., Journal of Bone and Mineral Research, Nov. 2004, vol. 19, No. 11:1749-1757.
Gallager, 1990, Metabolism, vol. 39, issue 4, supplement 1, Apr. 1990, pp. 27-29, abstract only.
DTP Datawarehouse Index Results, from http://dtp.nci.nih.gov/dtpstandard/servlet/dwindex?searchtype=NSC&outputformat=html&searchlist=366218 accessed Dec. 3, 2007.
In Vivo Models, http://dtp/nci.nih.gov/docs/invivo/invivomodels.html, accessed Dec. 3, 2007, p. 33 only of 55 provided.
NCI Communication re InVivo screening: email From: Daniel Zaharevitz[zaharevitz@dtpax2.ncicrf.gov], Sent: Tuesday, Dec. 4, 2007 5:37 PM, to: Gamett, Daniel C., Subject: Re: in vivo screen data, p. 1 of 1.
NCI in Vivo Screening Data http://dtp.nci.nih.gov/dtpstandard/servlet/InvivoScreen?testshortname=tumor+PS... Accessed Dec. 3, 2007.
U.S. Appl. No. 60/963,774, Donegan, James J. et al.
Clark, Robert D., Consensus Scoring for Ligand/Protein Interactions, Journal of Molecular Graphics and Modeling, 2002;20:281-295.
Dale, Trevor C., Signal Transduction by the WNT Family of Ligands, Biochem. J., 1998;329:209-223.
Daniels, Danette L., Molecular Cell, 2002;10:573-584.
Logan and Nusse, The WNT Signaling Pathway in Development and Disease, Annu. Rev. Cell. Dev. Biol., 2004;20:781-810.
Kelly, Olivia G., The WNT Co-Receptors LRP5 and LRP6 Are Essential for Gastrulation in Mice, Development 2004;131:2803-2815.
Mi and Johnson, Role of the Intracellular Domains of LRP5 and LRP6 in Activating the WNT Canonical Pathway, Journal of Cellular Biochemistry, 2005;95:328-338.
Mi, K.,The Journal of Biological Chemistry, 2006;281(8):4787-4794.
Zeng, X., A Dual-Kinase Mechanism for WNT Co-Receptor Phosphorylation and Activation, Nature, 2005;438(8):873-877.

\* cited by examiner

COMPOSITIONS AND METHODS FOR THE STIMULATION OR ENHANCEMENT OF BONE FORMATION AND THE SELF-RENEWAL OF CELLS

REFERENCE TO RELATED PATENT APPLICATIONS

This application is related to the patent application entitled "Compositions and Methods for Bone Formation and Bone Remodeling", by Dan Wu, et. al, filed on May 19, 2004, and its entire contents is hereby incorporated by reference, in its entirety.

FIELD OF THE INVENTION

The present invention relates to compositions and methods comprising Dickkopf-2 (Dkk2), a protein antagonist and/or inhibitor of Wnt proteins, for stimulating or enhancing mineralization and for stimulating the renewal of cells. Dkk2 acts to stimulate bone formation independently of Wnt proteins which may be inhibited and/or antagonized by Dkk2. Specifically, Dkk2 stimulates osteoblast differentiation, and therefore mineralization. Dkk2 also plays a role in the differentiation and self-renewal of hematopoietic stem cells and mesenchymal stem cells, particularly in osteoblastogenesis and osteoclastogenesis.

All patents, patent applications, patent publications, scientific articles, and the like, cited or identified in this application are hereby incorporated by reference in their entirety in order to describe more fully the state of the art to which the invention pertains.

BACKGROUND OF THE INVENTION

Human and mouse genetic evidence indicates that the Low density lipoprotein Receptor Protein (LRP), a Wnt co-receptor LRP-5[1,2], plays an important role in bone remodeling[3-6]. In addition, canonical Wnt proteins and activated β-catenin stimulate Alkaline Phosphatase (AP) activity of osteoblast-like cells[3,7]. However, the precise roles of the canonical Wnts and their antagonist Dickkopf (Dkk) molecules in the regulation of osteogenesis remain unclear. Dkk proteins are believed to function as negative regulators in osteogenesis. Dkk proteins are cysteine-rich secreted proteins that have been shown to be negative regulators of Wnt signaling. Four Dkk proteins have been identified in humans and are referred to as Dkk1, Dkk2, Dkk3 and Dkk4.

There is a correlation between LRP5 mutations and bone mass, based on human studies, thereby suggesting that LRP5 plays a critical role in the regulation of bone development[3-6]. This conclusion was confirmed by the study of mice in which the LRP-5 gene is disrupted, as well as in mice in which the high bone mass mutation of LRP5 was targeted to bone tissue[8,9]. Evidence also indicates that canonical Wnts are classified based on either their ability to stabilize β-catenin to activate LEF-1/TCF transcriptional activity[10], or on their ability to stabilize β-catenin to stimulate AP activity of osteoblast-like cells[3,7]. Together, all these findings suggest the involvement of canonical Wnt signaling in the regulation of osteogenesis. However, the mechanisms by which the canonical Wnt proteins regulate osteogenesis remain unclear.

Human bone marrow contains hematopoietic stem cells (HSCs) and mesenchymal stem cells (MSCs), among others. In vivo, stem cells have the characteristic of self-regeneration, allowing them to renew themselves indefinitely. This renewal feature has not always been found to occur when the cells are grown in vitro. MSCs differentiate into mesenchymal tissue lineages, such as osteoblasts, chondrocytes, adipocytes, and others, whereas HSCs serve as precursors for multiple cell lineages, including blood cells. Mononuclear precursor cells are derived from early hematopoietic stem cells, and osteoclasts form from the fusion of mononuclear precursor cells. Natural Killer T (NKT) cells, a subset of T lymphocytes, are also derived from hematopoietic stem cells. Upon stimulation through their T cell receptors (TCRs), NKT cells produce high levels of immunoregulatory cytokines, which in turn regulate immune responses, such as the suppression of autoimmunity, tumor rejection and tissue graft associated response.

MSCs, also known as marrow stromal cells, osteoprogenetor cells and osteoblast stem cells, serve as feeder layers that regulate the microenvironment for the maintenance, expansion or renewal of hematopoietic stem cells. Osteoblasts are stromal cells that have been shown to produce hematopoietic growth factors at their endosteal surfaces, thereby playing an important role in HSC development. It has been demonstrated that increasing the number of osteoblasts results in a boost in HSC populations[1*,2*].

Wnt3a, one of the canonical Wnts, has been shown to function in the direct regulation of stem cell growth, particularly hematopoietic stem cell growth. Wnt3a is involved in numerous developmental events, including the proliferation and self-renewal of stem cells.[3*,4*] Wnt3a also functions in the indirect regulation of hematopoietic stem cell lineage development through stromal cells. (Yamane, T. et al, Wnt Signaling Regulates Hemopoiesis Through Stromal Cells") It has been demonstrated that exogenous Dickkopf-1 (Dkk-1), an antagonist of Wnt, increases the proliferation of cultured mesenchymal stem cells. When a Dkk1 antibody was added, the proliferation of cultured mesenchymal stem cells decreased. The same Dkk1 effect was also observed in cultured MG-63 osteosarcoma cells.[5*,7*] However, the in vivo and in vitro effects of the Dkk proteins on hematopoietic stem cells, NKT cells and other types of stem cells have been unknown. The present invention describes the effect of Dkk proteins on various stem cells.

SUMMARY OF THE INVENTION

The present invention is directed to methods and compositions that address several problems related to bone remodeling, such as osteoporosis and other bone diseases. The invention also provides for the use of compositions to aid in the healing of fractures or other injuries or abnormalities of bone. In particular, the invention provides a process for stimulating or enhancing osteoblast mineralization in a mammalian subject comprising administering to the subject an effective amount of Dkk protein, a Wnt inhibitor, or a Wnt antagonist.

The invention further provides for gene therapy methodologies for clinical conditions characterized by insufficient mineralization comprising administering an effective amount of Dkk, a Wnt inhibitor or a Wnt antagonist, or by causing an increase in the expression of Dkk, a Wnt inhibitor or a Wnt antagonist.

In other aspects of the invention, gene expression, detection and quantification of Dkk, Wnt inhibitors, Wnt antagonists or related proteins serve as potential diagnostic methods for a variety of bone diseases.

Another aspect of the invention provides for mutant or altered forms of Dkk proteins, Wnt inhibitors or Wnt antagonists, including those that selectively stimulate bone cell differentiation but lack the ability to inhibit Wnt signaling.

The present invention also provides for other modifications such as fusion proteins of Dkk, which show enhanced specific targeting or biological activity in stimulating mineralization.

The invention further provides for the development of Dkk-related transgenic mice or experimental animals that over-express Dkk2. Such animals may serve as models for the in vivo evaluation and characterization of mutant or altered Dkk and related fusion proteins.

The invention is also directed to methods and compositions that address the effect of Wnt, Dkk, a Wnt inhibitor, a Wnt antagonist or a related protein on the self-renewal of hematopoietic stem cells, NKT cells and other self-renewing stem cells in vivo and in vitro.

Yet another aspect of the present invention provides for the development of Dkk proteins for therapeutic applications, such as bone marrow transplantation and expansion of hematopoietic stem cells, NKT cells and other stem cells in vivo and in vitro.

BRIEF DESCRIPTION OF THE DRAWINGS

FIG. 1A shows bone marrow stromal (BMS) isolated from 3 month old mice carrying a GFP transgene controlled by the 2.3 Kb CollA1 promoter which were infected with control or Wnt1 adenovirus or treated with Wnt3a CM. Cells were stained for AP activity after 5 days, or fixed and stained for mineralization at the time indicated (b, Von Kossa silver stain; c, Alizarrin Red stain); FIG. 1B is a Northern analysis of the expression of osteogenic markers OC and BSP at different stages of differentiation.

FIG. 2A provides Real Time RT-PCR results which show that the expression of Dkk1 and Dkk2 increases and the expression of Wnt7b increases at first, and then decreases during BMS cell differentiation. FIG. 2B, FIG. 2C & FIG. 2D are mouse long bone section, in situ hybridization pictures. FIG. 2B shows that Dkk1 is mainly expressed in osteocytes. FIG. 2C shows that Dkk2 is mainly expressed in osteoblasts. FIG. 2D shows that Wnt7b is expressed in osteoblasts.

FIG. 3A and FIG. 3B show that during osteogenic cell differentiation, the expression of both Wnt5a and Wnt5b first increases, and then decreases.

FIG. 4A shows that the GFP level in the Dkk1 treated culture is much less than in the control (FIG. 4B). These results indicate that osteoblast differentiation is inhibited by Dkk1 protein at the time indicated (FIG. 4C).

FIG. 5A shows that mineralization does not increase or decrease in BMS cultures transduced with Wnt1 Adenovirus, as compared to that in BMS culture treated by control Adenovirus (FIG. 5B) at the time indicated (FIG. 5C).

FIG. 6A is a Northern Blot result and shows that Dkk2 mRNA level is significantly increased in MC3T3 cell culture transduced with Wnt1 Adenovirus and that Dkk2 mRNA was not detected in the MC3T3 cell culture treated with control Adenovirus. FIG. 6B shows that GFP in BMS cells from 2.3 Col-GFP mice may be turned on within 24 hours by the addition of Wnt3a CM. This result indicates that canonical Wnt can stimulate osteoblast differentiation. FIG. 6C shows pictures of BMS cell cultures from 2.3 Col-GFP mice immunostained with Dkk2 antibody. Expressed Dkk2 protein is co-localized with 2.3 Col-GFP, an osteoblast differentiation marker.

FIG. 7A shows relative Dkk2 expression levels as determined by Real Time RT-PCR at various time points of differentiation in MC3T3 cells transduced with SupDkk2 or control vector. FIG. 7B shows mineralization of MC3T3 cells transduced with SupDkk2. FIG. 7C shows the mineralization of MC3T3 cells transfected with a control vector. These results indicate that there is strong correlation between Dkk2 expression and mineralization. FIG. 7D shows BMS cultures transduced with Dkk2-expressing Adenovirus and stained with Xylenol Orange at the indicated time (FIG. 7F). FIG. 7E shows BMS cultures infected with a control Adenovirus and stained with Xylenol Orange at the indicated time. (FIG. 7F). A unique pattern of calcification was observed in Dkk2-transduced cell culture.

FIG. 9d, FIG. 9e and FIG. 9f are pictures with penetrating light under the microscope.

DETAILED DESCRIPTION OF THE INVENTION

Figure 1:
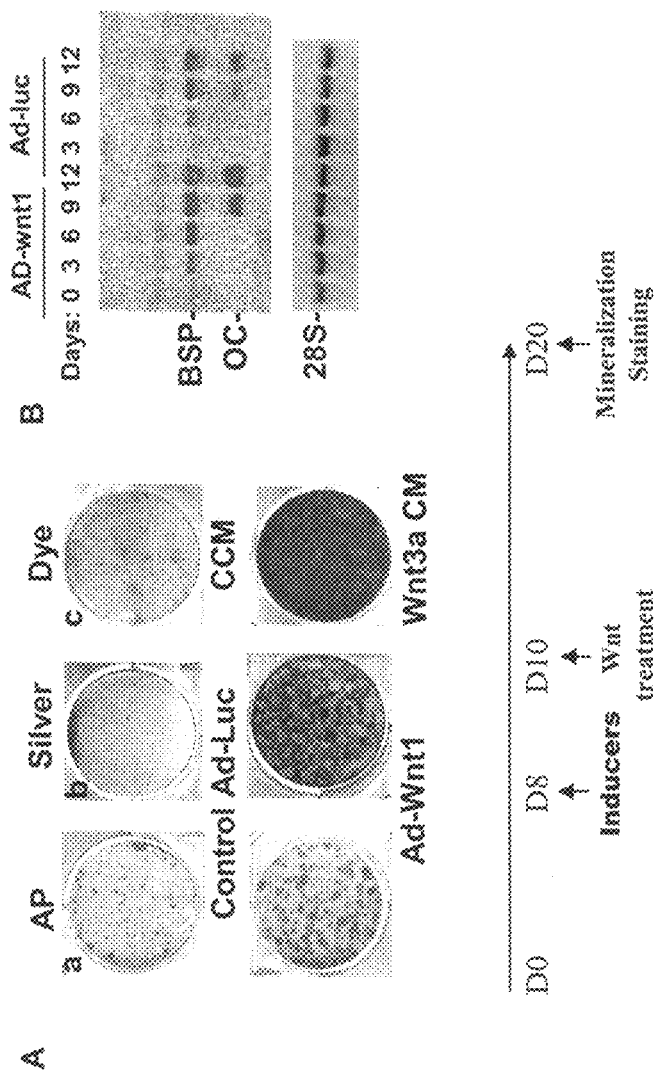
FIG. 1 illustrates canonical Wnt stimulation of osteogenic cell proliferation and differentiation.

The present invention provides methods and compositions for the treatment of bone diseases, bone fractures, bone injuries and other bone abnormalities. This is accomplished by administering an effective amount of Dkk protein, Wnt inhibitor, Wnt antagonist, or any other related protein to a mammalian subject to cause the stimulation or enhancement of mineralization.

Dkk may comprise Dkk1, Dkk2, Dkk3, Dkk4, or any combination thereof. Dkk protein also comprises a protein independent of any Wnt which may be inhibited or antagonized by any Dkk protein, a protein acting independently of its role in the regulation of canonical Wnt signaling, or an enzymatic homologue, unrelated protein with analogous functions, or homologue of Dkk. A Wnt antagonist comprises Dkk, a protein, sugar, chemical, lipid, glycoprotein, glycolipid, polypeptide, nucleic acid, small molecule, Wnt1, Wnt2, Wnt3, Wnt3a, Wnt4a, Wnt5a, Wnt5b, Wnt6, Wnt7a, Wnt7b, Wnt7c, Wnt8, Wnt8a, Wnt8b, Wnt8c, Wnt10a, Wnt10b, Wnt11, Wnt14, Wnt15, Wnt16, or at least one of the following proteins or at least one fragment of the following protein: a Dkk protein, a crescent protein, a cerebrus protein, an axin protein, an Frzb protein, a glycogen synthase kinase protein, a T-cell factor protein, a dishevelled protein or an sFRP3 protein. A Wnt inhibitor may comprise Dkk, a protein, sugar, chemical, lipid, glycoprotein, glycolipid, polypeptide, nucleic acid, small molecule, Wnt1, Wnt2, Wnt3, Wnt3a, Wnt4a, Wnt5a, Wnt5b, Wnt6, Wnt7a, Wnt7b, Wnt7c, Wnt8, Wnt8a, Wnt8b, Wnt8c, Wnt10a, Wnt10b, Wnt11, Wnt14, Wnt15, Wnt16, or at least one of the following proteins or at least one fragment of the following protein: a Dkk protein, a crescent protein, a cerebrus protein, an axin protein, an Frzb protein, a glycogen synthase kinase protein, a T-cell factor protein, a dishevelled protein or an sFRP3 protein. The proteins or protein fragments may be biologically derived from natural sources, or obtained using recombinant DNA methods. For the treatment of human subjects, it is preferred that the proteins or protein fragments are derived from non-human sources. Potential immunological reactions may be minimized or eliminated by the treatment of the subject with immunosuppressive reagents or by the application of a reagent specific immune manipulation as described in patent application Ser. No. 09/356,294, entitled "Novel Selective Immune Down Regulation (SIDR) Mediated Translation Processes for Preventing or Treating Diseases in a Subject, and Compositions of Matter Comprising Trained or Programmed Cells, Tissues or Organs Useful for SIDR Establishment.", by Rabbani, E., et. al, filed on Jul. 16, 1999.

In a preferred embodiment of the invention, a specific Dkk protein, Dkk2 protein, is used for the treatment of bone diseases, fractures, injuries and abnormalities. Dkk2 displayed enhanced specific targeting ability and enhanced biological activity in stimulating or enhancing mineralization. In prior art, Dkk1 and Dkk2 were shown to acts as inhibitors of Wnt, resulting in the inhibition of bone formation, stimulation, enhancement or remodeling. Specifically, when Dkk1 (a stronger inhibitor) or Dkk2 (a weaker inhibitor) was added before the pre-osteoblast stage, bone stimulation or enhancement did not occur. The present invention shows that when Dkk2 (a stronger stimulant) or Dkk1 (a weaker stimulant) is added, there is stimulation or enhancement of bone formation. Dkk2 stimulated the mineralization of cultured osteoblasts through a pathway independent of its role as an antagonist of Wnt signaling. Dkk2 is believed to function through this non-Wnt pathway since neither Dkk1 (a stronger Wnt antagonist) nor Axin (an intracellular Wnt inhibitor), nor Frzb were observed to stimulate mineralization. Osteoblast differentiation was accompanied by the up-regulation of the expression of Dkk2. In addition to stimulating the differentiation of osteoblasts, Dkk2 also inhibited the Wnt produced.

It was observed that Wnt proteins stimulate the self-renewal of osteoblast progenitor cells. The Wnt proteins, including Wnt7b, Wnt3a and Wnt1, were shown to not only stimulate osteogenic cell renewal, but to also stimulate osteoblast differentiation by activating the osteoblast-specific 2.3 Kb CollA1 promoter. The present invention provides that the canonical Wnts, including Wnt7b, Wnt3a and Wnt1, play an important role in osteoblast differentiation. When Wnt was added to pre-osteoblasts, the pre-osteoblasts differentiated into osteoblasts. When Wnt was added at the stage when Dkk2 could stimulate or enhance mineralization, to mature osteoblasts in vitro, mineralization was not stimulated or enhanced by Wnt.

Osteoblasts are located in a niche where stem cells are also found. In this niche, hematopoeitic stem cells renew themselves continuously. Since osteoblasts produce Wnt, particularly Wnt 7b, and Wnt7b has been shown to boost stem cells in vivo, [25,26] osteoblasts stimulate the self-renewal of hematopoietic stem cells[27,28]. When Wnt, or osteoblasts that produce Wnt were added to stem cells in vitro, the cells showed self-renewal. Since Dkk2 was shown to inhibit Wnt, when Dkk2 was added to these cells, renewal of the cells ceased, and they began to differentiate.

The present invention has shown that Dkk2 increases the number of osteoblasts in vivo. Since osteoblasts have been shown to stimulate the self-renewal of hematopoietic stem cells[27,28], then Dkk2 should also cause stem cells to renew through a different mechanism or pathway.

Clinical conditions which are characterized by insufficient mineralization may be treated through the use of genetic engineering, genetic manipulation or other gene therapy methodologies. These methods include the introduction of new genes, the elimination of genes present in the organism, or the introduction of additional copies of genes present in a subject that result in an increase or decrease of expression. For example, if the desired result is an increase or overexpression of Dkk, a Wnt inhibitor, a Wnt antagonist, or a related protein, then mineralization is stimulated or enhanced. This was shown when transgenic mice were developed that over-expressed Dkk2. The present invention allows these altered mice to serve as models for the in vivo evaluation and characterization of mutant or altered Dkks, Wnt inhibitors, or Wnt antagonists, and related fusion proteins. These fusion proteins have been shown to enhance specific targeting or biological activity in stimulating or enhancing mineralization. These mutant, altered or fused proteins include those that selectively stimulate bone cell differentiation or proliferation but lack the ability to inhibit Wnt signaling.

Genetic manipulation may be carried out either through transient expression or by a permanent introduction of new genetic characteristics. Manipulation may be carried out on the cells ex vivo followed by the introduction of the cells into the subject. Conversely, the manipulation may be carried out in vivo. Methods for carrying out transient expression ex vivo include the application of oligonucleotides or polynucleotides to a cell culture in vitro or infection by vectors that are commonly used for transient expression, such as adenoviruses. Methods that may be used for permanent expression in vitro include ligand mediated uptake, as described in patent application Ser. No. 08/574,443, entitled "Novel Property Effecting and/or Property Exhibiting Compositions for Therapeutic and Diagnostic Uses", by Rabbani, E. et. al, filed on Dec. 15, 1995, the transformation of cell cultures by expression vectors with selectable markers, or infection with viral vectors. Examples of these include retrovirus and Adeno-Associated Viruse (AAV) based vectors. Tropisms for the introduction of material into the appropriate target cells in vitro or in vivo may be changed using well-known techniques.

When transgenic mouse models were developed that caused a reduction or elimination in Dkk2 expression, the end result was a decrease in bone density. Dkk2 was therefore found to play an important role in the regulation of osteogenesis in both the in vitro cell culture model and the in vivo transgenic mouse model Furthermore, a decrease in both osteoblasts and osteoclasts was observed in Dkk2 knock-out mice. This decrease, in turn, resulted in a decrease in the subsequent production of any Dkk2 cells. This indicates that Dkk2 is essential in both osteoblastogenesis and osteoclastogenesis. Since osteoclasts and osteoblasts are derived from hematopoeitic stem cells (HSCs) and mesenchymal stem cells (MSCs) respectively, and the number of hematopoeitic stem cells present are parallel to the number of osteoblast cells present, a decrease in osteoblasts or osteoclasts results in a decrease in HSCs or MSCs. It has been shown that Dkk is required for the proliferation and re-entry into the cell cycle of human adult stem cells from bone marrow. Since Dkk2 protein displays an important role in the development and proliferation of lineages derived from hematopoietic and mesenchymal stem cells, it appears that Dkk2 is involved in the proliferation, differentiation and self-renewal of HSCs and MSCs. Since it has also been shown that Wnt7b is upregulated during osteoblast differentiation, Wnt7b also has an effect on the differentiation and proliferation of cells. It has also recently been shown that under certain conditions, human NKT $V_{\alpha24}$ cells can be activated to differentiate or proliferate in vitro.[8*,9*] Therefore, Dkk proteins, Dkk derivatives, Wnt inhibitors, Wnt antagonists, and other related proteins could be developed as therapeutic agents for the renewal of hematopoeitic stem cells, NKT cells, and other types of cells.

These therapeutic agents may be used in certain applications such as bone marrow transplantation by introducing them directly at the site of disease, fracture or abnormality. They may also be used indirectly, by combining the therapeutic agent(s) and the cells (removed from the subject) in vitro, thereby allowing the cells to proliferate, and then reintroducing the original cells and the proliferated cells into the subject. Specifically, the desired cells may be removed from the diseased subject and placed in vitro with an effective amount of Dkk, Wnt inhibitor, Wnt antagonist, or related protein sufficient to stimulate the renewal of the desired cells, accompanied by a feeder layer. The feeder layer may comprise mesenchymal stem cells, stromal cells or other types of cells that promote cell growth or differentiation. The renewed cells are then reintroduced into the subject. The cells may also be removed from another subject, renewed, and reintroduced into the diseased subject.

The present invention also describes compositions and methods for the treatment of infectious diseases. These diseases comprise any type of viral mediated or immune drug mediated hepatitis, bacterial infections, viral infections, fungal infections, or parasitic infections. The viral infection may be an HBV, HCV or HIV infection. The treatment comprises the in vitro renewal of transduced cells. The cells are transduced in order to introduce at least one gene resistant to the specific disease that is being treated.

A preferred embodiment comprises obtaining CD34+ cells from a subject infected with a virus and transducing the cells in vitro so as to introduce a gene resistant to the virus. The transduced cells are then cultured in conditions comprising providing a feeder layer and an amount of Dkk, Wnt inhibitor, Wnt antagonist or related protein sufficient to stimulate the renewal of the transduced cells in vitro. When the cells have proliferated, they are reintroduced into the infected subject.

The present invention also provides in vitro screening assays for enzymatic homologues, unrelated proteins with analogous functions, or homologues of Dkk proteins, Wnt inhibitors or Wnt antagonists. A preferred embodiment provides MC3T3 cells transduced with Dkk2 expression retrovirus in a first test tube, MC3T3 cells transduced with a control vector in a second test tube, and MC3T3 cells transduced with an enzymatic homologue, an unrelated protein with analogous functions, or a homologue of a Dkk protein, a Wnt inhibitor, or a Wnt antagonist in a third test tube. The amount of mineralization in each test tube is determined. If the amount of mineralization in the first test tube is greater than the amount of mineralization in the second test tube, and approximately the same amount of mineralization as in the third test tube, the enzymatic homologue, unrelated protein with analogous functions, or homologue of a Dkk protein, Wnt inhibitor or Wnt antagonist functions to enhance or stimulate mineralization.

Another embodiment provides an in vitro screening assay for enzymatic homologues, unrelated proteins with analogous functions, or homologues of Dkk proteins, Wnt inhibitors or Wnt antagonists comprising BMS culture cells transduced with Dkk2 expression adenovirus in a first test tube, BMS culture cells transduced with a control vector in a second test tube, and BMS culture cells transduced with an enzymatic homologue, an unrelated protein with analogous functions, or a homologue of a Dkk protein, a Wnt inhibitor, or a Wnt antagonist in a third test tube. The amount of mineralization in each test tube is determined. If the amount of mineralization in the first test tube is greater than the amount of mineralization in the second test tube, and approximately the same amount of mineralization as in the third test tube, the enzymatic homologue, unrelated protein with analogous functions, or homologue of a Dkk protein, Wnt inhibitor or Wnt antagonist functions to enhance or stimulate mineralization.

Yet another embodiment for the in vitro screening of an enzymatic homologue, an unrelated protein with analogous functions, or a homologue of a Dkk protein, a Wnt inhibitor or a Wnt antagonist which is administered to a mammalian subject to treat a disease, provides regulatory, immune-regulatory or NKT cells and a feeder layer in a first tube, regulatory, immune-regulatory or NKT cells and an enzymatic homologue, an unrelated protein with analogous functions, or a homologue of a Dkk protein, a Wnt inhibitor, or a Wnt antagonist in a second test tube, and regulatory, immune-regulatory or NKT cells, Dkk protein and a feeder layer in a third tube. The amount of cell renewal or proliferation in each of the three tubes is then determined. If the amount of cells in the second tube are greater than the amount of cells in the first tube, and approximately the same amount of cells in the third tube, then the enzymatic homologue, unrelated protein with analogous functions, or homologue of a Dkk protein, Wnt inhibitor or Wnt antagonist functions to cause cells to renew or proliferate.

Another embodiment for the in vitro screening of an enzymatic homologue, an unrelated protein with analogous functions, or a homologue of a Dkk protein, a Wnt inhibitor or a Wnt antagonist comprises (1) transducing MC3T3 cells with a control vector; and (2) transducing MC3T3 cells with a retrovirus comprising the enzymatic homologue, unrelated protein with analogous functions, or homologue of a Dkk protein, a Wnt inhibitor or a Wnt antagonist. The transduced cells are then stained for mineralization with Alizarrin Red. If the control (1) does not show mineralization, and (2) does, then that enzymatic homologue, unrelated protein with analogous functions, or homologue of a Dkk protein, a Wnt inhibitor or a Wnt antagonist functions to enhance or stimulate mineralization.

A preferred embodiment for an in vitro screening assay comprises the use of BMS culture cells instead of MC3T3 cells in the aforesaid procedure, and staining with Xylenol Orange instead of Alizarrin Red.

The present invention also provides for an in vitro screening assay where the addition of an enzymatic homologue, an unrelated protein with analogous functions, or a homologue of a Dkk protein, a Wnt inhibitor or a Wnt antagonist to Dkk2 knock-out mice results in the enhancement or stimulation of mineralization.

Materials and Methods

BMS Cell Cultures and the Induction of Osteogenic Differentiation

BMS cell cultures from 3 month old mice were generated as previously described[11]. The BMS cells were briefly cultured at the density of $10 \times 10^6$ cells/well in α-medium containing 100 U/ml Penicillin, 100 U/ml Streptomycin and 10% FCS. After 5 days, the cultures were fixed with 4% paraformaldehyde at 4 C.° for 10 minutes. Osteoblast colony formation was visualized by staining for AP (Sigma Diagnostics). Once the cells reached confluency, they were induced to undergo osteogenic differentiation in the presence of 10 nM Dexamethasone, 8 mM β-glycerophosphate, and 50 ug/ml Ascorbic Acid. Media was changed every two days. Mineralization was visualized by staining the cultures with Von Kossa silver nitrate or Alizarrin Red after fixation.

Bone Marrow Cells and the Induction of Osteoclast Differentiation

Cells from the bone marrow of mice were seeded in 48 well plates at the density of $5 \times 10^5$ cells/well in α-medium containing antibiotics, 10% FCS, 30 ng/ml MCSF and 60 ng/ml RANKL. Medium was changed every two days. On the 6$^{th}$ day, osteoblast cells were fixed with 4% paraformaldehyde at 4 C.° for 10 minutes and visualized by TRAP staining (Sigma Diagnostics).

Osteoblast Culture From Mouse Calvariae:

Mouse calvariae was removed from 5-8 day old mice, washed twice with PBS and digested with PBS solution containing 0.05% Trypsin, 0.2 mM EDTA and 0.5 mg/ml Collagenase P, to release osteoblast cells. Osteoblast cells were collected by centrifugation and seeded in 6 well plates at the density of $2 \times 10^5$ cells/well in the DMEM with 100 U/ml Penicillin, 100 U/ml Streptomycin, 10% FCS and 1% non-Essential Amino Acids. After the 7th day, the cells became confluent. The medium was changed to α-medium containing antibiotics, 10% FCS, 5 mM β-glycerophosphate, and 25 ug/ml Ascorbic Acid. The medium was changed daily. Mineralization was visualized by staining the living cell cultures with 20 nM Xylenol Orange.

Immunostaining

BMS cells were seeded onto coverslips in 6-well plates. The coverslips were fixed at varying time points and blocked by the Blocking Reagent from Vector Laboratories. The cells were then permeabilized, and stained with an anti-Dkk2 monoclonal antibody followed with Rodamine-conjugated secondary antibody.

QPCR and Northern Analysis

Total RNA was isolated using the TRIzol reagent (Invitrogen), according to the manufacturer's instructions. For QPCR analysis, RNA was reverse-transcribed by the SuperScript™ First-Strand Synthesis System for Real Time RT-PCR (Invitrogen). QPCR was carried out using the QuantiTect™ SYBR Green PCR kit (Qiagen) on a DNA Engine OPTICON™ (MJ Research Inc.) instrument. β-actin was used as an internal reference for each sample. Using a formula previously described[24], the relative change in mRNA levels was normalized against the p-actin mRNA levels. For Northern analysis, RNA (10 µg) was separated by agarose gel and transferred to Nylon membranes, which were probed with [$^{32}$P] labeled probes.

SiRNA and Dkk Expression

The H1 promoter based siRNA production unit was inserted into a retroviral vector, which was then used to produce a retrovirus. MC3T3 cells were infected with the retrovirus. Cells stably transduced with the vector were selected by Hygromycin (Calbiochem-Novabiochem Co.). Hygromycin-resistant clones were pooled for the study.

For the over-expression of Wnt1, Dkk1, Dkk2 and sFRP3 in BMS cells, Adenovirus containing the Wnt1, mDkk1, mDkk2 or sFRP3 expression cassette were generated. BMS cell cultures were transduced with the Adenoviruses and mineralization was visualized by staining the living cell cultures with 20 nM Xylenol Orange.

In Situ Hybridization

The full-length coding region of Dkk1, Dkk2 and Wnt7b were used to synthesize anti-sense and sense probes. The probes were labeled with Digoxigenin using an RNA Labeling Kit (Roche, Indianapolis, Ind., USA). Sections of the tibia from a 3-week old mouse were dewaxed, rehydrated and fixed again with 4% paraformaldehyde. The sections were treated with 2% glycine and Proteinase-K and acetylated using an acetic anhydride/TEA solution, followed by hybridization with a digoxygenin-labelled probe. After washing the sections with 50% formamide, 5×SSC, and 5% SDS for 30 minutes at 70° C. twice and 50% formamide, 2×SSC for 30 minutes at 65° C., the sections were incubated with anti-digoxigenin-alkaline phosphatase antibody followed by Nitro Blue Tetrazolium/4-bromo-5-chloro indolylphosphate, which yields a purple blue color. The sections were also counterstained with methyl green (nuclei) and orange G (cytoplasma).

BMD Measurement

A DKK2 knockout mouse model was created. 2 month old mice were examined for their bone mineralization density using dual-energy X-ray absorptionometry (DXA) with the PIXImus small animal DEXA system (GE-Lunar, Madison, Wis.).

EXAMPLES

1. Stimulation of Osteoblast Mineralization by Canonical Wnt.

Bone marrow stromal (BMS) cells were isolated from 3-month-old mice carrying a Green Fluorescent Protein (GFP) transgene controlled by the 2.3 Kb CollA1 promoter (2.3 Col-GFP),[11] the expression of which is limited to osteoblasts and osteocytes. GFP can therefore be used as a marker of osteoblast cells. On the 10th day, BMS cultures were infected with either a control adenovirus expressing luciferase or an adenovirus expressing Wnt1. On the 20$^{th}$ day, the cultures were fixed and stained for mineralization with Von Kossa silver stain and Alizarrin Red stain. The expression of two widely used markers for osteoblast differentiation, bone sailioprotein (BSP) and osteocalcin (OC), were also examined using Northern Blot analysis.

Transduction with the Wnt1 expressing adenovirus or treatment of Wnt3a conditioned medium (CM) led to increases in mineralization of primary BMS cultures in the presence of the osteogenic inducers, Dexamethasone, Ascorbic acid, and β-glycerophosphate (FIG. 1A). This increase in mineralization was due to an increase in osteocytes, which act as terminal differentiation markers. The expression of both BSC and OC markers also increased in cells infected with the Wnt1 adenovirus (FIG. 1B).

2. Canonical Wnt Stimulates AP Activity in Osteogenic Cells.

Bone marrow stromal (BMS) cells were isolated from 3-month-old mice carrying 2.3 Col-GFP. On the $10^{th}$ day, BMS cultures were infected with either control adenovirus expressing luciferase or an adenovirus expressing Wnt1. On the $15^{th}$ day, the cells were subsequently stained for AP activity.

As shown in FIG. 1A-a, the BMS culture that was infected with Wnt1 expressing adenovirus (Ad-Wnt1) appeared to show more AP staining than the culture infected with the control virus. Counting the number of colonies revealed that Wnt-1 infection resulted in increases in the size rather than the number of the colonies. This result is consistent with previous findings that canonical Wnts stimulate AP activity[3,7] (probably by stimulating the proliferation of osteoblast progenitor cells) and that LRP-5-deficiency decreases the proliferation of osteoblast progenitor cells.[8]

3. Identification of Endogenous Canonical Wnt in BMS Culture.

To identify the expression pattern of Wnt in the BMS cultures, the mRNA of 19 different Wnts from primary BMS cultures was measured by Real Time RT-PCR. RNA was extracted from mice BMS cultures at different time points. Real Time RT-PCR was used to measure the mRNA level of the 19 Wnts. The expression of both Dkk1 and Dkk2 in BMS cultures was also examined by Real Time RT-PCR.

Wnt7b cDNA was also cloned using Real Time RT-PCR and verified to be a canonical Wnt by a LEF-1-luciferase reporter assay. In order to identify the expression of Wnt7b, Dkk1 and Dkk2 in vivo, in situ hybridization was performed on mouse long bone sections using cDNA of Wnt7b, Dkk1 and Dkk2 as probes.

Figure 2:
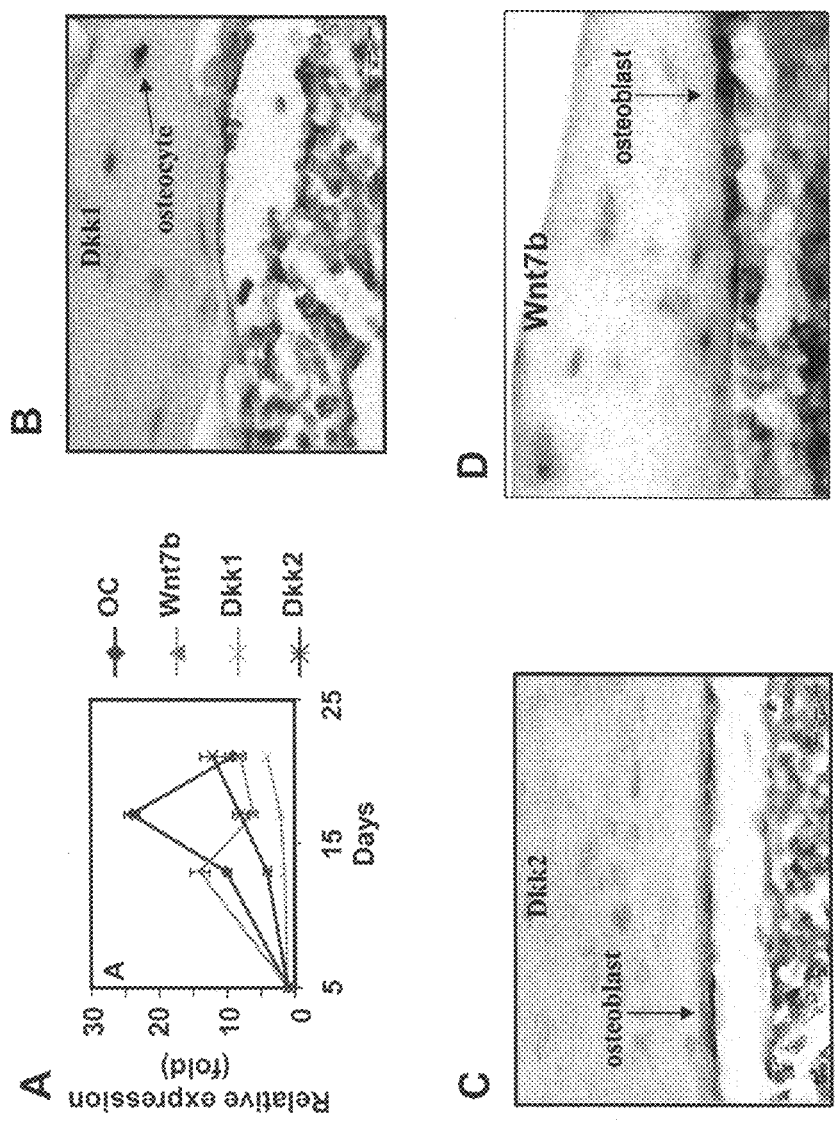
FIG. 2 illustrates Dkk1, Dkk2 and Wnt7b expression in osteogenic cells.

The results indicated that among canonical Wnts, only Wnt1 and Wnt7b RNA were detectable in primary BMS cultures. The expression of Wnt1 was barely detectable and its amount did not change during the entire differentiation cycle. In contrast, the expression level of Wnt7b changed significantly during differentiation. The Wnt7b mRNA peaked on the $8^{th}$ day after the addition of differentiation media on the $5^{th}$ day, and then decreased to a lower level, as shown in FIG. 2A. The level of Dkk2 mRNA increased significantly during differentiation, while the level of Dkk1 mRNA increased only at the terminal stage of differentiation (FIG. 2A).

Figure 3:
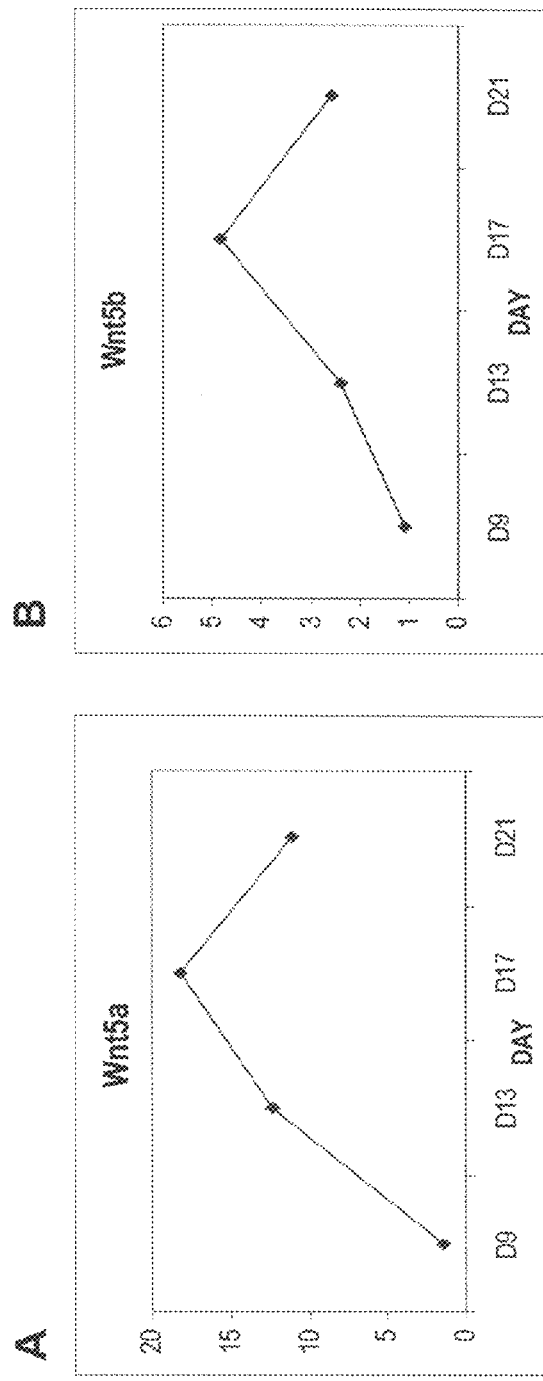
FIG. 3 illustrates Wnt5a and Wnt5b expression during BMS cell differentiation using Real Time RT-PCR.

In situ hybridization results showed Dkk1 expression in osteocytes (FIG. 2B) and Dkk2 and Wnt7b expression in osteoblasts. During osteogenic cell differentiation, Wnt5a and Wnt5b significantly increased, as shown in FIG. 3A & FIG. 3B.

4. The Antagonistic Effect of Dkk1 on Wnt Functions in Osteogenic Cells.

Figure 4:
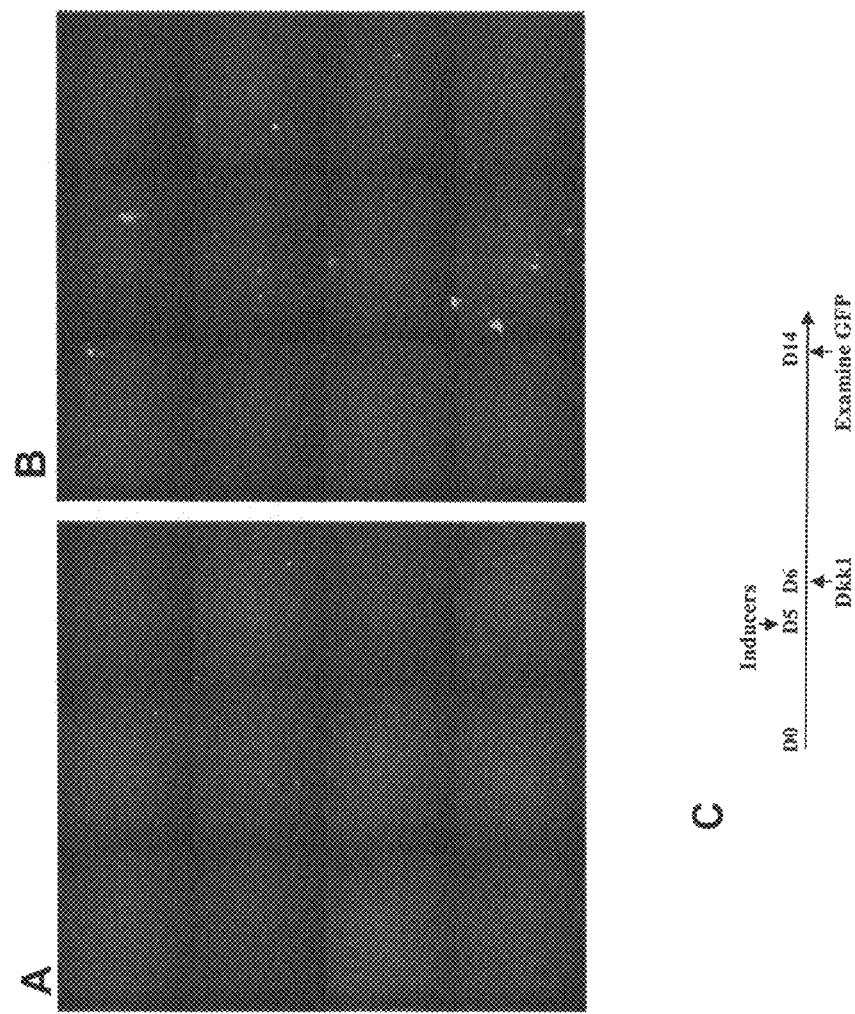
FIG. 4 illustrates that Dkk1 can inhibit osteoblast differentiation at the early stage. BMS cultures from 2.3 CollA1 mice were treated with either recombinant Dkk1 protein (1 μM) or with control buffer. The expression of GFP was examined at the indicated times.

BMS cells were isolated from 3-month-old mice carrying 2.3 Col-GFP. On the $6^{th}$ day, recombinant Dkk1 protein (1 µM) or control buffer was added to the BMS culture. GFP expression was examined using fluorescent microscopy. Cells treated with Dkk1 protein showed a decrease in GFP expression (FIG. 4A) compared to the control cells (FIG. 4B). A strong correlation was observed between GFP expression and mineralization in mice carrying a GFP transgene controlled by the 2.3 Kb CollA1 promoter[11]. The decrease of GFP expression by Dkk1 protein indicates that the early stage of osteogenic cell differentiation which is mediated by canonical Wnt may be blocked by Dkk1.[1,12,13]

5. Canonical Wnt does not Stimulate Mineralization at Late Stage of Osteoblast Differentiation.

BMS cells were isolated from 3-month-old mice carrying 2.3 Col-GFP. On the $15^{th}$ day, BMS culture was infected with either Adenovirus carrying Wnt1 or control Adenovirus. On the $17^{th}$ day, BMS culture was stained for mineralization by Xylenol Orange.

Figure 5:
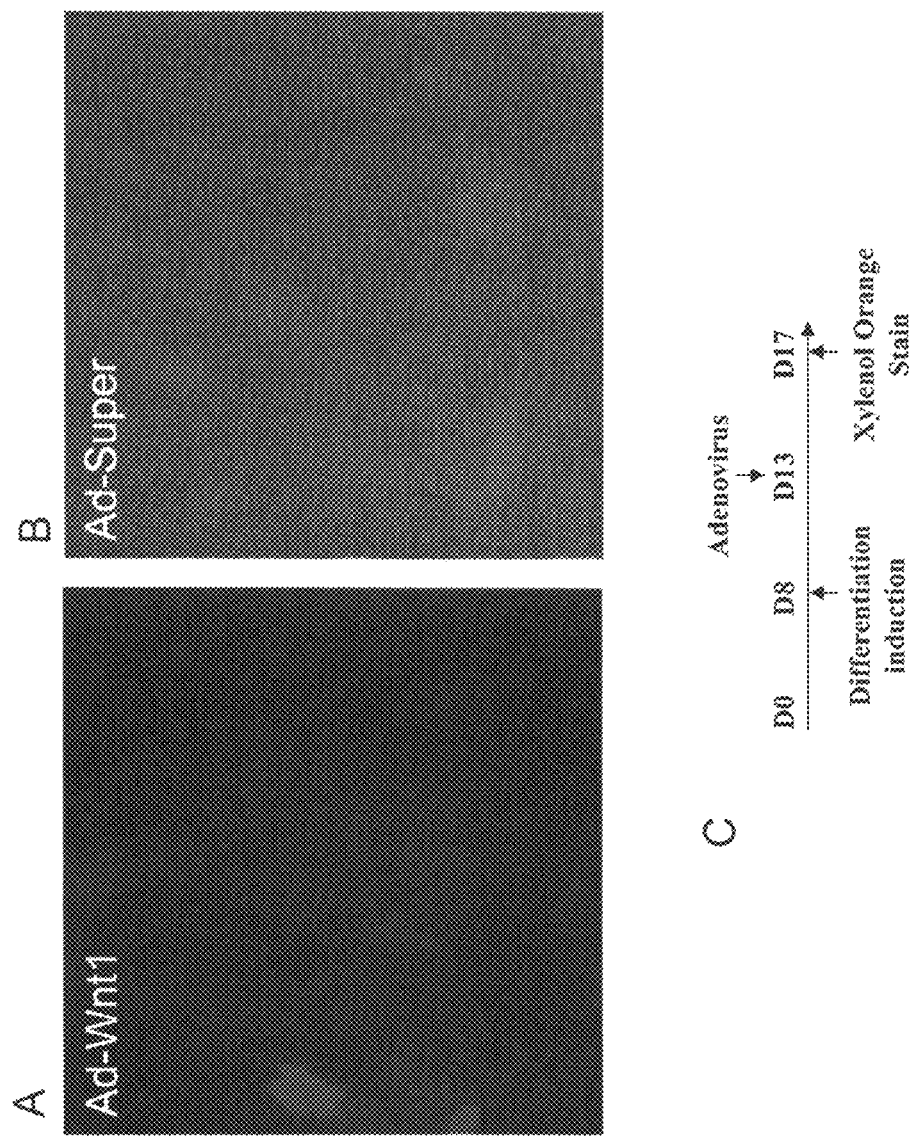
FIG. 5 illustrates that canonical Wnt does not affect the late stage of osteoblast differentiation.

The results indicated that at the late stage of BMS culture, the addition of canonical Wnt does not have any effect on mineralization, as shown in FIG. 5.

6. Canonical Wnt Upregulates Dkk2 Expression During the Differentiation of Osteogenic Cells.

MC3T3 cells, originally derived from calvarial cultures, can be induced to undergo osteogenic differentiation. Although mineralization of MC3T3 cells was not as robust as that observed in BMS cultures, many of the osteoblast differentiation markers, including OC, BSP and collagen I, showed expression patterns similar to those of the primary cultures. MC3T3 cells were transduced with either Wnt1-Adenovirus or control Adenovirus. The cellular mRNA was isolated at different time points during differentiation. Northern blot analysis was used to analyze Dkk2 expression.

BMS cell cultures from 2.3 Col-GFP mice were treated with Wnt3a CM or control CM on the $10^{th}$ day and GFP was examined on the $11^{th}$ day. BMS cells were seeded to cover slips for assaying. When GFP was expressed, cells were immunostained with anti-Dkk2 monoclonal antibody and Rodanmine (Red) labeled second anti-mouse antibody. GFP and Rodanmine were examined by confocal microscopy.

Figure 6:
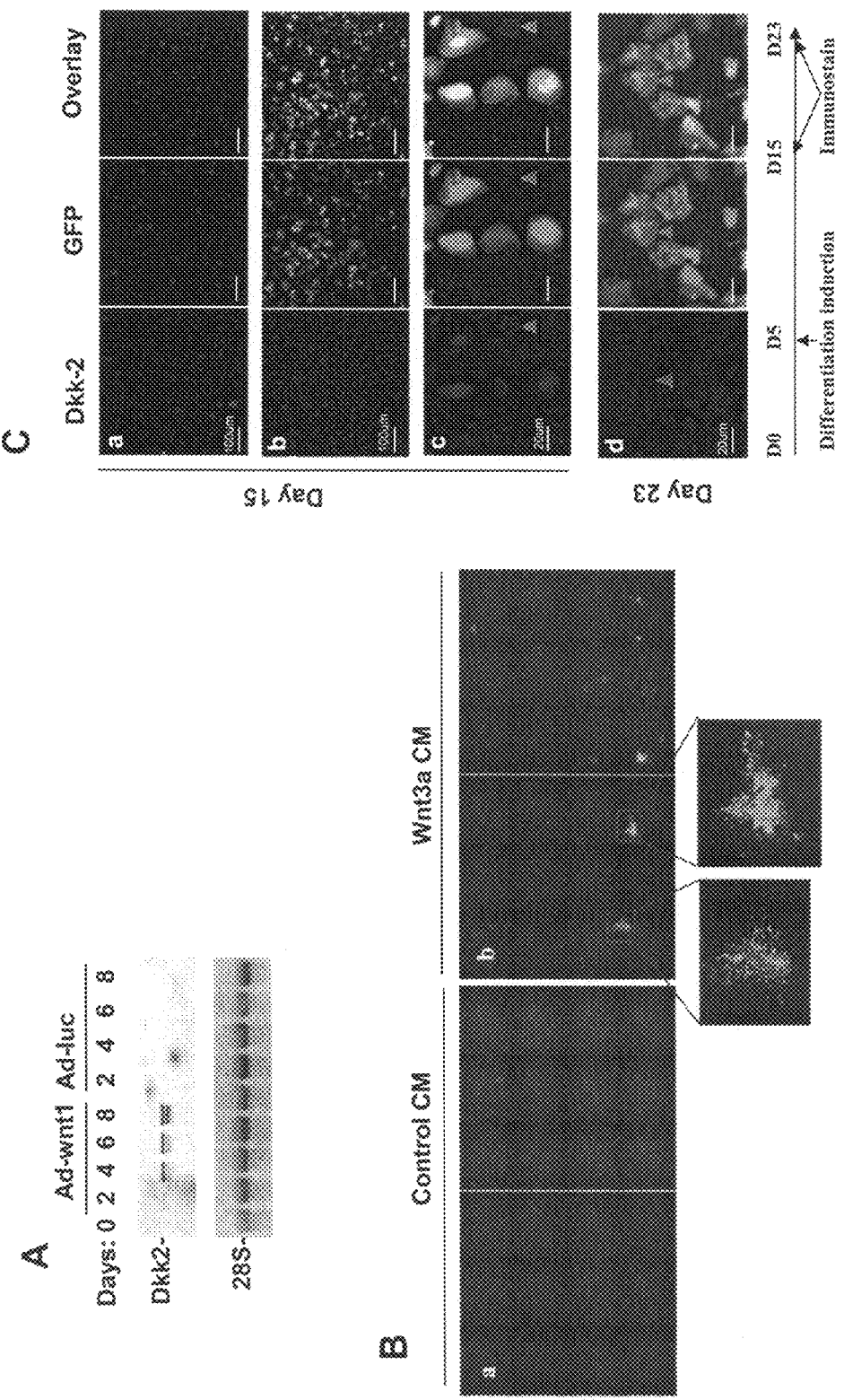
FIG. 6 illustrates that Dkk2 is upregulated by canonical Wnt in osteoblast cells.

The level of Dkk2 mRNA in Wnt1 transduced MC3T3 cells significantly increased compared to that in control cells (FIG. 6A). FIG. 6B shows that canonical Wnt can turn on the 2.3 Col-GFP. Dkk2 expression is co-localized with the 2.3 Col-GFP (FIG. 6C).

7. Dkk2 Stimulates Mineralization During the Late Stage of Cultured Osteogenic Cells.

To examine the role of Dkk2 in early osteoblast growth and differentiation, siRNA was used to knock down the expression of Dkk2[14]. An in vivo siRNA production strategy was adopted in which the H1RNA polymerase III promoter drove the synthesis of hairpin duplex siRNA specifically targeting Dkk2[15] (SupDkk2). MC3T3 cells were stably transduced with Dkk2 siRNA, producing retrovirus or control retrovirus and induced to differentiate. Dkk2 expression levels were measured at different time points by Real Time RT-PCR and mineralization was monitored by Von Kossa silver stain.

BMS cultures were induced to differentiate on the $8^{th}$ day and transduced with either Dkk2 expressing Adenovirus or control Adenovirus on the $13^{th}$ day, and stained for mineralization with Xylenol Orange on the $17^{th}$ day.

Figure 7:
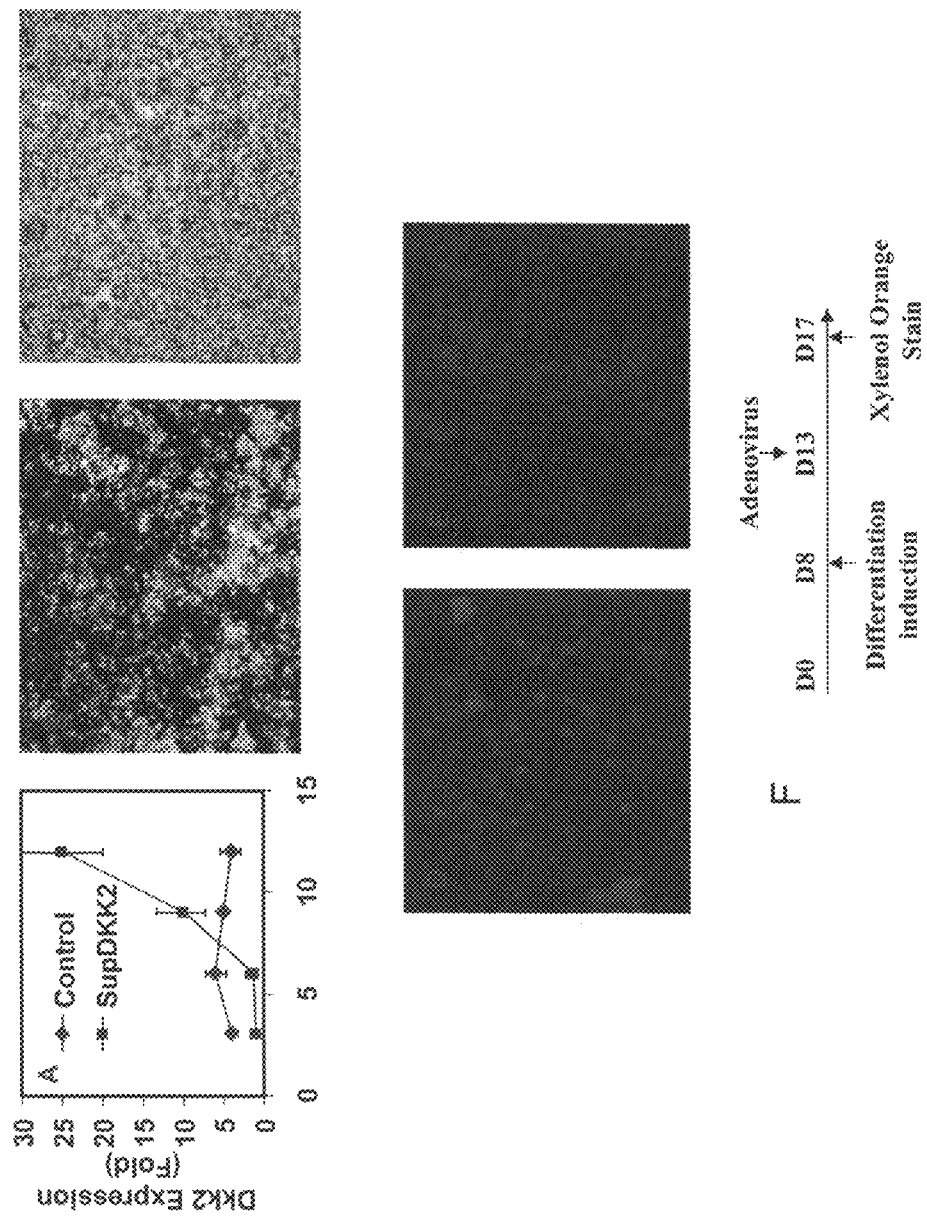
FIG. 7 shows Dkk2 stimulation of mineralization.

MC3T3 cells stably transduced with SupDkk2 (SupDkk2 cells) showed lower levels of Dkk2 mRNA (about one-third of that of the control cells) up to the $6^{th}$ day post differentiation induction (FIG. 7A). Unexpectedly, Dkk2 mRNA levels started to elevate in SupDkk2 cells on the $9^{th}$ day, and on the $12^{th}$ day, Dkk2 mRNA levels in SupDkk2 cells were 5 fold greater than that in MC3T3 cells stably transfected with a control siRNA vector (FIG. 7A). In contrast, there were no significant changes observed in the expression levels of Dkk2 in control MC3T3 cells during differentiation (FIG. 7A). SupDkk2 cells started to show mineralization approaching the $20^{th}$ day, and in a few days after that, showed a great increase in mineralization. (FIG. 7B). The non-transduced MC3T3 cells and those containing the control vector only showed background mineralization, even when they were assayed 35 days later (FIG. 7C). SupDkk2 MC3T3 cells more closely resembled the primary BMS cultures than the control MC3T3 cells in terms of both Dkk2 expression patterns and mineralization abilities. These results can be explained as that in MC3T3 cells, the inhibition of Dkk2 expression by siRNA could increase the canonical Wnt signaling activity, which normally inhibited by Dkk. Such an increase of Wnt signaling upregulates the Dkk2 expression leading to eventual escape from siRNA suppression. This high level of Dkk2 causes the MC3T3 to further differentiate.

The over-expression of Dkk2 in BMS cells transduced with Adenovirus results in the stimulation of mineralization, as shown in FIG. 7D, compared to the lack of mineralization shown by BMS cells transduced with a control Adenovirus (FIG. 7E).

8. The Effect of Wnt Inhibitor sFRP3 on Mineralization in Osteoblasts.

sFRP3 acts as a soluble Wnt-binding protein that antagonizes Wnt signaling. Its use here aids in observing its effect on mineralization.[35,36] BMS culture was transduced with either sFRP3 expressing Adenovirus or control Adenovirus on day 13 and stained for mineralization with Xylenol Orange on day 17.

Figure 8:
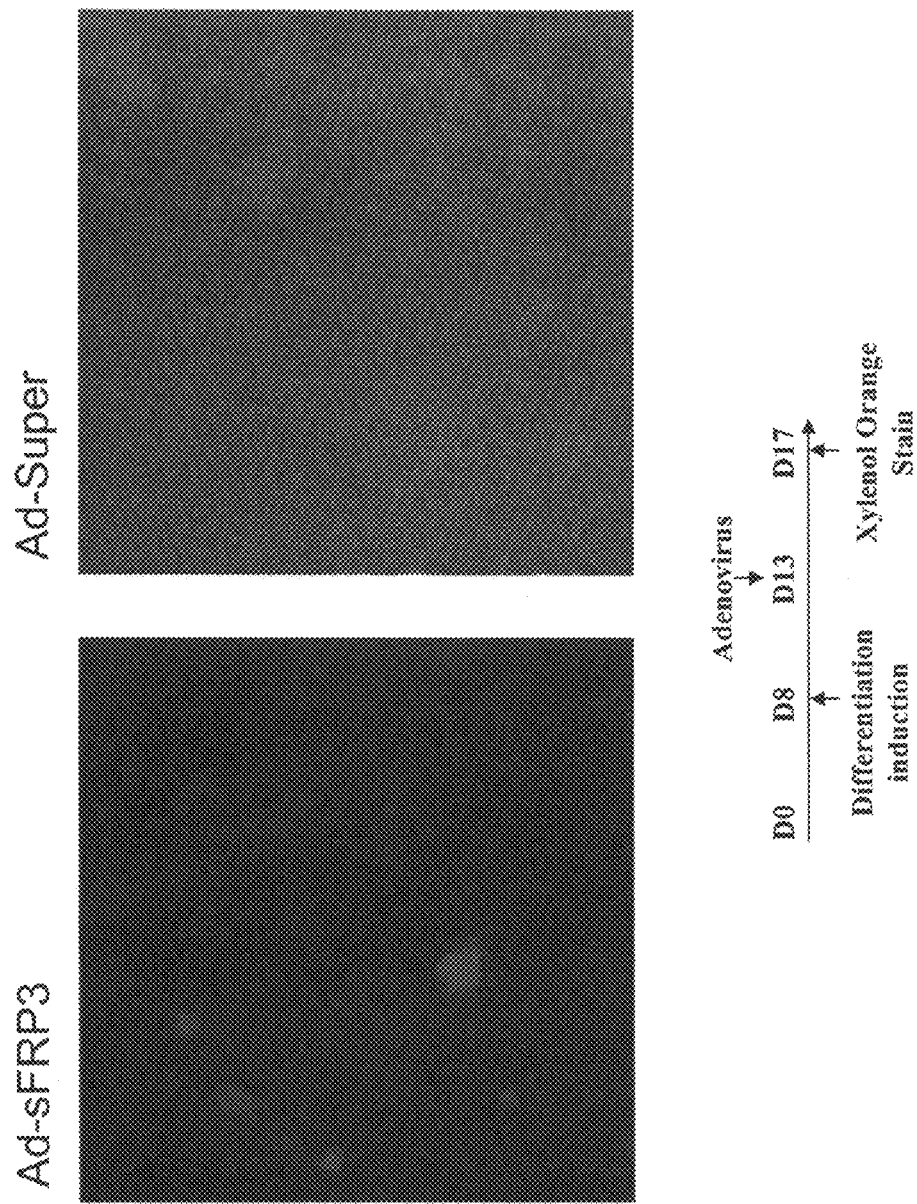
FIG. 8 shows that sFRP3, a Wnt inhibitor, cannot stimulate mineralization. BMS culture was treated with either sFRP3 expressing Adenovirus or control Adenovirus. The unique calcification pattern observed in FIG. 7E was not seen here.

The results indicated that there was no difference in mineralization between BMS cells transduced with sFRP3 expressing Adenovirus and BMS cells transduced with control Adenovirus. It appears that sFRP3 does not have any effect on the mineralization in BMS cell culture at certain osteoblast stage, whereas Dkk2 can stimulate mineralization at that stage. This shows that at this stage, the inhibition of Wnt does not affect mineralization (FIG. 8).

9. Bone Density Decreases in Dkk2 Knockout Mice.

Total bone mineral density was measured at the age of 55 days in both wild type male mice and DKK2 knockout male mice by dual-energy X-ray absorptionometry (DXA) with the PIXImus small animal DEXA system (GE-Lunar, Madison, Wis.).

Table 1 shows that the total bone density of Dkk2 knockout mice is 7.286% less than the total bone density in wild type mice. These results indicate that Dkk2 plays an important role in bone formation during development.

TABLE 1

Male Mice Total Bone Mineral Density (BMD)

| Wild Type (+/+) ($g/cm^2$) | DKK2 Knockout (−/−) ($g/cm^2$) | % | P Value |
|---|---|---|---|
| 0.05046 (N = 17) | 0.04678 (N = 17) | 7.286 | 0.00056 |

10. Mineralization Decreases in Osteoblast Cell Cultures from Dkk2 Knockout Mice.

Osteoblast cell culture was obtained from mice calvariae (wild type and Dkk2 knockout). On the $6^{th}$ day, the culture was induced to differentiate by the addition of 1 mM Ascorbic Acid and 5 mM β-glycerophosphotate to the medium. On the $15^{th}$ day, the cell culture was stained for mineralization with Xylenol Orange.

Figure 9:
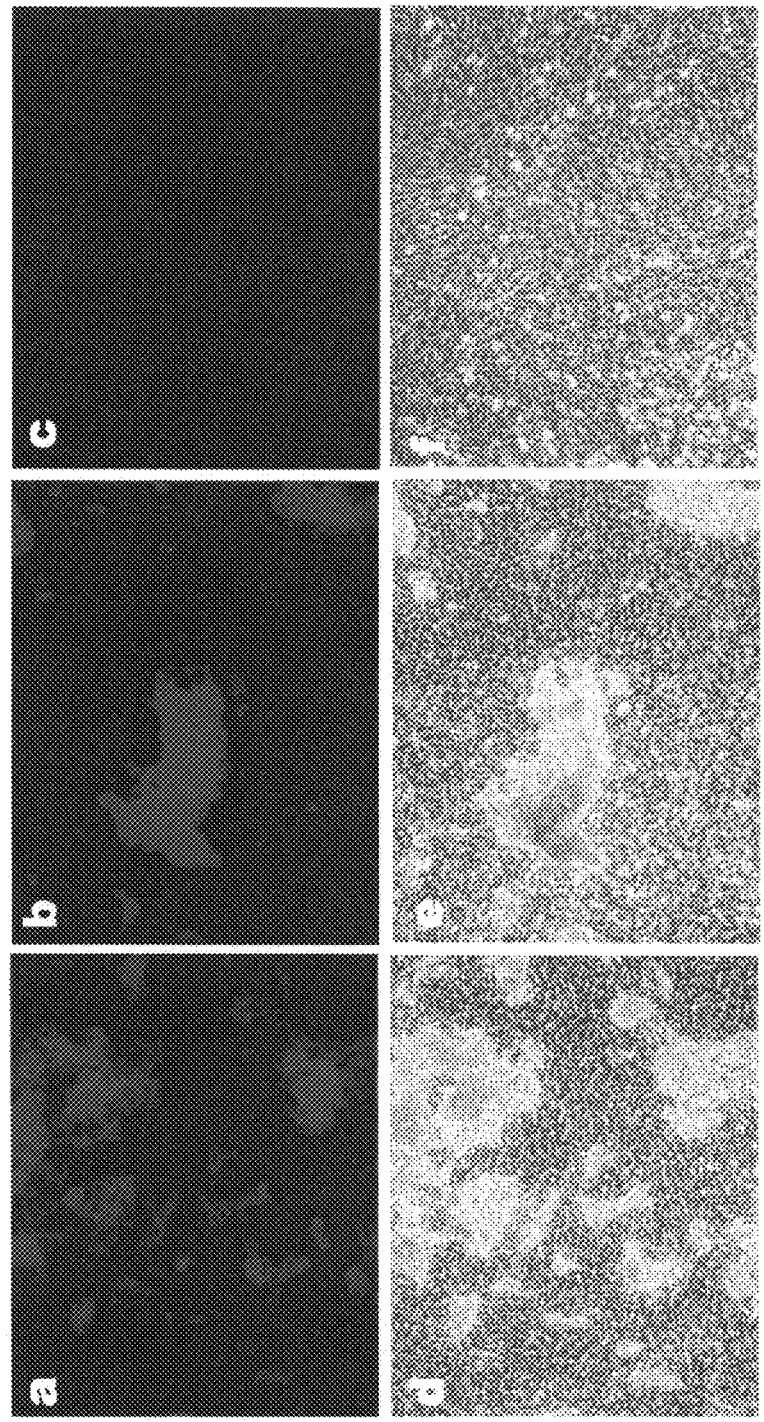
FIG. 9 illustrates that Dkk2 is required for mineralization. Osteoblast culture from mice calvariae was induced to differentiate. After 15 days, the cell culture was stained for mineralization with Xylenol Orange. Cell culture from wild type mice (FIG. 9a & FIG. 9d) or heterozygotic mice (FIG. 9b & FIG. 9e) showed strong mineralization. In contrast, the culture from Dkk2 knockout mice (FIG. 9c & FIG. 9f) did not show mineralization at all.

Up to the $15^{th}$ day, no mineralization was detected in the cell culture from Dkk2 knockout mice (FIG. 9c & FIG. 9f), whereas strong mineralization occurred in cell culture from wild type mice (FIG. 9a & FIG. 9d) or heterozygotic mice (FIG. 9b & FIG. 9e). FIG. 9d, FIG. 9e and FIG. 9f show mineralization pictures of penetrating light under the microscope.

11. The Formation of Both Osteoblasts and Osteoclasts Decreases in Dkk2 Knockout Mice.

BMS cell culture from wild type mice, Dkk2 knockout mice and heterozygotic mice was stained for AP activity on the $5^{th}$ day to monitor osteoblast colony formation. For osteoclast formation, Bone Marrow cell culture was induced to differentiate by the addition of 30 ng/ml Macrophage Colony-Stimulating Factor (M-CSF) and 60 ng/ml Receptor Activator of Nuclear factor KappaB (NF-kappaB) Ligand (RANKL) to the medium. On the $6^{th}$ day, osteoclast cells were stained by Tartrate-Resistant Acid Phosphatase (TRAP) and checked for multinucleated cell morphology under the microscope.

Figure 10:
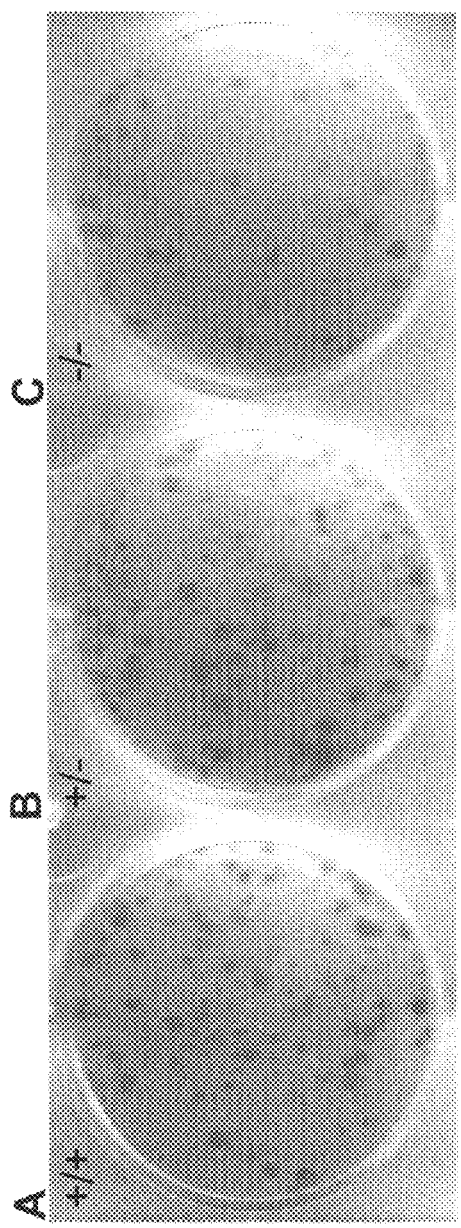
FIG. 10 shows that Dkk2 is a positive regulator of pre-osteoblast formation. BMS cell culture from wild type mice, Dkk2 knockout mice and heterozygotic mice were stained for AP on the 5$^{th}$ day to monitor osteoblast colony formation. The number of osteoblast colonies significantly decreased in the culture from Dkk2 knockout mice (FIG. 10A) compared to those in the culture from wild type (FIG. 10B) or heterozygotic mice (FIG. 10C).

The number of osteoblast colonies significantly decreased in the culture from Dkk2 knockout mice (FIG. 10C) compared to those in the culture from wild type (FIG. 10A) or heterozygotic mice (FIG. 10B).

Figure 11:
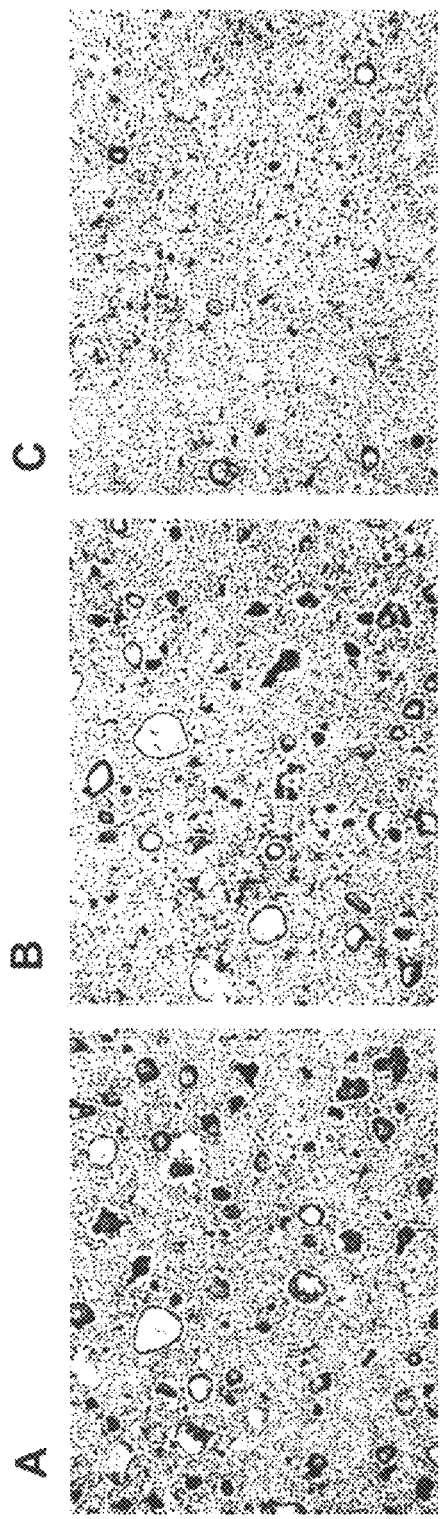
FIG. 11 illustrates the effect of Dkk2 on osteoclast formation. Cultures from the bone marrow of mice were induced to differentiate by the addition of M-CSF and RANKL to the medium. After 6 days, osteoclast cells were stained by Tartrate-Resistant Acid Phosphatase (TRAP) and checked for multinucleated cell morphology under the microscope. Osteoclast cell number was significantly decreased in the culture from Dkk2 knockout mice (FIG. 11C) as compared to the osteoclast cell number in the culture from wild type (FIG. 11A) or heterozygotic mice (FIG. 11B).
Figure 12:
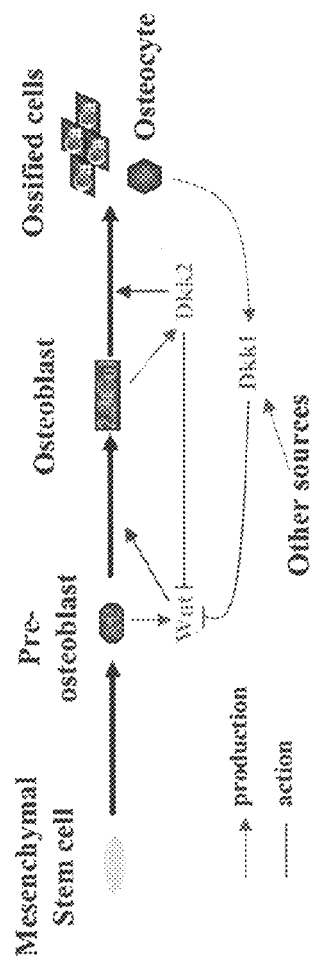
FIG. 12 is a cartoon showing a model for the role of canonical Wnt and Dkk proteins in the regulation of osteogenesis. Expression of the canonical Wnts (e.g., Wnt7b) increases in the pre-osteoblast stage. Canonical Wnts stimulate pre-osteoblast cell proliferation and differentiation into osteoblasts. During differentiation, Dkk2 expression is up-regulated, which in turn stimulates further differentiation. This Dkk2 effect is independent of its antagonism to Wnt signaling during the growth phase of osteoblast maturation.

Similarly, osteoclast cell number is also significantly decreased in the culture from DKK2 knockout mice (FIG. 11C) in comparison with those in the culture from wild type (FIG. 11A) or heterozygotic mice (FIG. 11B). The origin of osteoclasts is different from that of osteoblasts. The former is the progeny of hematopoeitic stem cells while the latter is the progeny of mesenchymal stem cells.

REFERENCES

1. Mao, B. et al. LDL-receptor-related protein 6 is a receptor for Dickkopf proteins. *Nature* 411, 321-5 (2001).
2. Mao, J. et al. Low-density lipoprotein receptor-related protein-5 binds to axin and regulates the canonical Wilt signaling pathway. *Mol Cell* 7, 801-9. (2001).
3. Gong, Y. et al. LDL receptor-related protein 5 (LRP5) affects bone accrual and eye development. *Cell* 107, 513-23 (2001).
4. Little, R. D. et al. A mutation in the LDL receptor-related protein 5 gene results in the autosomal dominant high-bone-mass trait. *Am J Hum Genet* 70, 11-9 (2002).
5. Boyden, 1. M. et al. High bone density due to a mutation in LDL-receptor-related protein 5. *N Engl J Med* 346, 1513-21 (2002).
6. Van Wesenbeeck, 1. et al. Six novel missense mutations in the LDL receptor-related protein 5 (LRP5) gene in different conditions with an increased bone density. *Am J Hum Genet* 72, 763-71 (2003).
7. Bain, G., Muller, T., Wang, X. & Papkoff, 1. Activated beta-catenin induces osteoblast differentiation of C3H10T1/2 cells and participates in BMP2 mediated signal transduction. *Biochem Biophys Res Commun* 301, 84-91 (2003).
8. Kato, M. et al: Cbfal-independent decrease in osteoblast proliferation, osteopenia, and persistent embryonic eye vascularization in mice deficient in Lrp5, a Wnt coreceptor. *J Cell Bioi* 157, 30314 (2002).
9. Babij, P. et al. High bone mass in mice expressing a mutant LRP5 gene. *J Bone Miner Res* 18, 960-74 (2003).
10. Wodarz, A. & Nusse, R. Mechanisms of Wnt signaling in development. *Annu. Rev. Cell Dev. Bioi.* 14, 59-88 (1998).
11. Kalajzic, 1. et al. Use of type I collagen green fluorescent protein transgenes to identify subpopulations of cells at different stages of the osteoblast lineage. *J Bone Miner Res* 17, 15-25 (2002).
12. Li, 1., Mao, J., Sun, 1., Liu, W. & Wu, D. Second cysteine-rich domain of Dickkopf-2 activates canonical Wnt signaling pathway via LRP-6 independently of dishevelled. *J Bioi Chern* 277, 5977-81 (2002).
13. Semenov, M. V. et al. Head inducer Dickkopf-1 is a ligand for Wnt coreceptor LRP6. *Curr Bioi* 11, 951-61 (2001).

14. Elbashir, S. M. et al. Duplexes of 21-nucleotide RNAs mediate RNA interference in cultured mammalian cells. *Nature* 411, 494-8 (2001).
15. Brummelkamp, T. R., Bernards, R. & Agami, R. A system for stable expression of short interfering RNAs in mammalian cells. *Science* 296, 550-3 (2002).
16. Kahler, R. A. & Westendorf, 1. J. Lymphoid enhancer factor-1 and beta-catenin inhibit Runx2 dependent transcriptional activation of the osteocalcin promoter. *J Bioi Chern* 278, 11937-44 (2003).
17. Mundlos, S. et al. Mutations involving the transcription factor CBF A1 cause cleidocranial dysplasia. *Cell* 89, 773-9 (1997).
18. Otto, F. et al. Cbfal, a candidate gene for cleidocranial dysplasia syndrome, is essential for osteoblast differentiation and bone development. *Cell* 89, 765-71 (1997).
19. Komori, T. et al. Targeted disruption of Cbfal results in a complete lack of bone formation owing to maturational arrest of osteoblasts. *Cell* 89, 755-64 (1997).
20. Ducy, P., Zhang, R., Geoffroy, V., Ridall, A. 1. & Karsenty, G. Osf2/Cbfa1: a transcriptional activator of osteoblast differentiation. *Cell* 89, 747-54 (1997).
21. Pandur, P., Lasche, M., Eisenberg, 1. M. & Kuhl, M. Wnt-II activation of a non-canonical Wnt signaling pathway is required for cardiogenesis. *Nature* 418, 636-41 (2002).
22. Wu, W., Glinka, A., Delius, H. & Niehrs, C. Mutual antagonism between dickkopf1 and dickkopf2 reguiates Wntlbeta-catenin signalling. *Curr Bioi* 10, 1611-4 (2000).
23. Itoh, K., Antipova, A., Ratcliffe, M. J. & Sokol, S. Interaction of dishevelled and Xenopus axinrelated protein is required for Wilt signal transduction. *Mol Cell Bioi* 20, 2228-38 (2000).
24. Pfaffl, M. W. A new mathematical model for relative quantification in real-time RT-PCR. *Nucleic Acids Res* 29, e45 (2001).
25. Zhang, J, et al. Identification of the haematopoietic stem cell niche and control of the niche size. Nature 425, 836-841 (2003)
26. Calvi, L, et al. Osteoblastic cells regulate the haematopoietic stem cell niche. Nature 425, 841-846 (2003)
27. Reya, T, et al. A role for Wnt signaling in self-renewal of haematopoietic stem cells. Nature 423, 409-414 (2003)
28. Willert, K, et al. Wnt proteins are lipid-modified and can act as stem cell growth factors. Nature 423, 448-452 (2003)
29. Gregory, C, et al. The Wnt signaling inhibitor Dickkopf-1 is required for re-entry into the cell cycle of human adult stem cells from bone marrow. The Journal of Biological Chemistry 278, 28067-28078 (2003)
30. Teitelbaum, S, et al. Genetic Regulation of osteoclast development and function. Nature Genetics 4, 638-649 (2003)
31. Prockop, D, et al. One strategy for cell and gene therapy: Harnessing the power of adult stem cells to repair tissues. PNAS 100, 11917-11923 (2003)
32. Brossay, L. et al. CD1d-mediated recognition of an α-galactosylceramide by natural killer T cells is highly conserved through mammalian evolution. J. Exp. Med. 188, 1521-1528 (1998)
33. Van del Viet, H., et al. Potent expansion of human natural killer T cells using α-galactosylceramide (KPN7000)-loaded monocyte-derived dendritic cells, cultured in the presence of IL-7 and IL-15. J. Immunol. Methods 247, 61-72 (2001)
34. Taichman R., et al. The Hematopoietic Microenvironment: Osteoblasts and The Hematopoietic Microenvironment. Hematol. 4(5):421-426 (2000)
35. Rattner A, et al. A family of secreted proteins contains homology to the cysteine-rich ligand-binding domain of frizzled receptors. PNAS. 94(7):2859-63. (1997)
36. Leyns L, et al. Frzb-1 is a secreted antagonist of Wnt signaling expressed in the Spemann organizer. Cell. 88(6): 747-56. (1997)
37. Yamane T., et al. Wnt Signaling Regulates Hemopoiesis through stromal cells. J. Immunology. 167:765-772. (2001)

The invention claimed is:

1. A method for stimulating or enhancing bone formation in a mammalian subject in need thereof, comprising administering to the mammalian subject at least one Dkk2 protein, a fragment of a Dkk2 protein capable of stimulating or enhancing bone formation, or a combination thereof.

2. A method for stimulating or enhancing osteoblast mineralization in a mammalian subject in need thereof, comprising administering to the mammalian subject at least one Dkk2 protein, a fragment of a Dkk2 protein capable of stimulating or enhancing osteoblast mineralization, or a combination thereof.

3. A method for regulating the proliferation of osteoblast progenitor cells in a mammalian subject in need thereof, comprising administering to the mammalian subject at least one Dkk2 protein, a fragment of a Dkk2 protein capable of regulating the proliferation of osteoblast progenitor cells, or a combination thereof.

4. A method for directly accelerating the differentiation of osteoblasts in a mammalian subject in need thereof, comprising administering to the mammalian subject at least one Dkk2 protein, a fragment of a Dkk2 protein capable of directly accelerating the differentiation of osteoblasts, or a combination thereof.

5. The method of any one of claims 1, 2, 3 or 4, wherein administering comprises inhalation, oral, intravenous, intraperitoneal, intramuscular, parenteral, transdermal, intravaginal, intranasal mucosal, sublingual, topical, rectal or subcutaneous administration, or any combination thereof.

6. The method of any one of claim 1, 2, 3 or 4, comprising administering the at least one Dkk2 protein.

7. The method of any one of claim 1, 2, 3 or 4, wherein said Dkk2 protein is administered to a bone.

8. The method of claim 7, wherein said bone has a disease, fracture, injury or abnormality.

9. The method of any one of any one of claim 1, 2, 3 or 4, wherein said Dkk2 protein or fragment is administered as a vector expressing a Dkk2 protein.

10. The method of claim 9, wherein said vector is a viral vector.

11. The method of claim 10, wherein said viral vector is a retrovirus, an adenovirus, or an adeno-associated virus.

12. The method of claim 9, wherein said vector is administered to a cell in vitro and the cell is transplanted into the mammalian subject.

13. The method of claim 12, wherein said cell is a hematopoietic stem cell, a mesenchymal stem cell, or a bone marrow stromal cell.

14. The method of claim 12, wherein said cell is from said mammalian subject.

15. The method of claim 12, wherein said cell is grown in the presence of a feeder layer prior to transplantation.

* * * * *